United States Patent
Escribá Ruiz et al.

(10) Patent No.: US 10,047,036 B2
(45) Date of Patent: Aug. 14, 2018

(54) METHOD FOR THE SYNTHESIS OF HYDROXY-TRIGLYCERIDES AND USES THEREOF FOR THE PREVENTION AND TREATMENT OF DISEASES

(71) Applicant: UNIVERSITAT DE LES ILLES BALEARS, Palma de Mallorca (ES)

(72) Inventors: Pablo Vicente Escribá Ruiz, Palma de Mallorca (ES); Xavier Busquets Xaubet, Calviá (ES)

(73) Assignee: UNIVERSITAT DE LES ILLES BALEARS, Palma de Mallorca (ES)

( * ) Notice: Subject to any disclaimer, the term of this patent is extended or adjusted under 35 U.S.C. 154(b) by 0 days.

(21) Appl. No.: 15/520,735

(22) PCT Filed: Oct. 21, 2015

(86) PCT No.: PCT/EP2015/074321
§ 371 (c)(1),
(2) Date: Apr. 20, 2017

(87) PCT Pub. No.: WO2016/062746
PCT Pub. Date: Apr. 28, 2016

(65) Prior Publication Data
US 2017/0313646 A1    Nov. 2, 2017

(30) Foreign Application Priority Data

Oct. 21, 2014 (EP) .................................... 14189696

(51) Int. Cl.
| | |
|---|---|
| *C07C 69/732* | (2006.01) |
| *C11C 3/00* | (2006.01) |
| *C11C 3/06* | (2006.01) |
| *C07C 51/367* | (2006.01) |
| *C07C 67/08* | (2006.01) |
| *C07C 67/327* | (2006.01) |

(52) U.S. Cl.
CPC .......... *C07C 69/732* (2013.01); *C07C 51/367* (2013.01); *C07C 67/08* (2013.01); *C07C 67/327* (2013.01); *C11C 3/00* (2013.01); *C11C 3/06* (2013.01)

(58) Field of Classification Search
CPC ...... C07C 69/732; C07C 51/367; C07C 67/08
See application file for complete search history.

(56) References Cited

U.S. PATENT DOCUMENTS

| | | | |
|---|---|---|---|
| 4,839,161 A | 6/1989 | Bowser et al. | |
| 6,537,787 B1 | 3/2003 | Breton | |
| 2004/0258743 A1* | 12/2004 | Compton | A61K 8/375 424/450 |
| 2011/0136906 A1 | 6/2011 | Escribá Ruiz et al. | |
| 2012/0108550 A1 | 5/2012 | Escribá Ruiz et al. | |
| 2014/0288176 A1 | 9/2014 | Escribá Ruiz et al. | |
| 2015/0297548 A1 | 10/2015 | Escribá Ruiz et al. | |

FOREIGN PATENT DOCUMENTS

| | | |
|---|---|---|
| CN | 103897284 A | 7/2014 |
| EP | 0261812 A1 | 3/1988 |
| EP | 1435235 A1 | 7/2004 |
| EP | 2374453 A1 | 10/2011 |
| EP | 2409963 A1 | 1/2012 |
| EP | 2774910 A1 | 9/2014 |
| WO | 03094625 A1 | 11/2003 |

OTHER PUBLICATIONS

Zheng, Chao.; "PVC plasticizer with low environmental pollution," Database CA; Chemical Abstracts Service, XP002737347, retrieved from STN Databse accession No. 2014:1092116, Jul. 2, 2014.
Ozaki, J.: "On the Nutritive Vlue of Synthetic Fats Containing Oxy-Fatty Acids," Proceedings of the Imperial Academy, 1926, pp. 341-344, vol. 2.
Guardiola-Serrano, F., et al.; "The Novel Anticancer Drug Hydroxytriolein Inhibits Lung Cancer Cell Proliferation via a Protein Kinase C—and Extracellular Signal-Regulated Kinase 1/2-Dependent Mechanism," Journal of Pharmacology and Experimental Therapeutics, 2015, pp. 213-224, vol. 354.
International Search Report, dated Jan. 26, 2016.

* cited by examiner

*Primary Examiner* — Pancham Bakshi
(74) *Attorney, Agent, or Firm* — Tristan A. Fuierer; Moore & Van Allen, PLLC

(57) ABSTRACT

The present invention relates to hydroxy-triglycerides, their synthesis, a pharmaceutical and/or nutraceutical composition which comprises at least one of said hydroxy-triglycerides, and a method which comprises the administration to a patient of a therapeutically effective quantity of at least one of said hydroxy-triglycerides or at least one of said pharmaceutical and/or nutraceutical compositions, for the prevention and/or treatment of at least one disease selected from cancer, metabolic/cardiovascular diseases, and/or neurological/inflammatory diseases.

12 Claims, 10 Drawing Sheets

A

B

C

A

B

C

D

C

D

A

B

METHOD FOR THE SYNTHESIS OF HYDROXY-TRIGLYCERIDES AND USES THEREOF FOR THE PREVENTION AND TREATMENT OF DISEASES

CROSS-REFERENCE TO RELATED APPLICATIONS

This application is filed under the provisions of 35 U.S.C. § 371 and claims the priority of International Patent Application No. PCT/EP2015/074321, filed on 21 Oct. 2015 entitled "METHOD FOR THE SYNTHESIS OF HYDROXY-TRIGLYCERIDES AND USES THEREOF FOR THE PREVENTION AND TREATMENT OF DISEASES" in the name of Pablo Vicente ESCRIBÁ RUIZ et al., which claims priority to European Application No. 14189696.9 filed on 21 Oct. 2014, both of which are hereby incorporated by reference herein in their entirety.

FIELD OF THE INVENTION

The present invention relates to a compound, the method for producing said compound and the use of said compound for the preparation of a medicine to be used in the prevention and/or treatment of at least one disease whose common aetiology is based on alterations (of any origin) of the lipids of the cell membrane or of the lipids circulating in blood or plasma such as, for example, alterations in the level, in the composition or in the structure of said lipids. Likewise, for pathologies in which regulation of the membrane lipid structure and composition induces the reversion of the pathological condition. Furthermore, the present invention relates to a compound for use in the prevention and/or treatment of at least one disease.

At the same time, the present invention relates to a pharmaceutical and/or nutraceutical composition which comprises said compound and a method for the preparation thereof. Finally, the present invention relates to a method for the prevention and/or therapeutic treatment of at least one disease in humans and animals which comprises administration to the patient of a therapeutically effective amount of said compound or said pharmaceutical and/or nutraceutical composition.

Thus, the present invention, due to its broad spectrum of application, can be encompassed in the field of nutrition, medicine and pharmacy in general.

STATE OF THE ART

Oils are important nutrients in the human diet. In their majority, oils are triglycerides formed by one glycerol molecule which on each carbon atom carries one oxygen joined to one acyl moiety (instead of a hydrogen radical), wherein each molecule of the triglyceride carries three equal or different acyl moieties which result in the esterification of each one of the three hydroxyl moieties of the glycerol with one carboxyl moiety of a fatty acid.

Between 10% and about 80% of human energy requirements are covered by fats in general and oils in particular (Prentice, 1998). Different epidemiological studies have demonstrated that certain types of oils have beneficial effects on human health, while others have negative effects on health (Flickinger and Huth, 2004; West et al., 2005; Hunter et al., 2010; Lawrence, 2013; Michas et al., 2014). In particular, oils rich in long chain trans-monounsaturated or saturated fatty acids (e.g., palm oil) have negative effects on metabolic and cardiovascular health (Stender and Dyerberg, 2004). On the contrary, oils rich in monounsaturated (e.g., olive oil) or polyunsaturated (e.g., fish oil) fatty acids have positive effects on health (Sánchez-Quesada et al., 2013; Grosso et al., 2013; Berge et al., 2014; Mayneris-Perxachs et al., 2014; Michas et al., 2014; McDonald et al., 2014; Whayne, 2014; Gultekin et al., 2014). More specifically, in these and other works it has been observed that the prolonged intake of olive oil, rich in ω-9 fatty acids, and/or fish, rich in co-3 fatty acids, reduce blood pressure, prevent diabetes, atherosclerosis, obesity, inflammation, pain, Alzheimer's disease and other neurodegenerative processes, cancer and different dyslipidaemias, among other pathological disorders (Hart et al., 2013; Shah, 2013; Kovisto et al., 2014 and previous references). In general, the intake of these oils, rich in triglycerides (the triglycerides content in these oils is more than 90%) have very positive important preventive effects on human health, but their pharmacological activity for the treatment of diseases is, in general, very limited. For example, neither olive oil nor fish oil is prescribed to treat cancer due to its reduced efficacy once a tumor has appeared. The molecular bases of these positive effects lie in their capacity to regulate circulating lipids and the composition and structure of the cell membrane (Escribá et al., 2008). However, given that they are used as cell fuel, their therapeutic effect is not relevant and their effects are circumscribed within prevention rather than the treatment of different diseases.

Cell membranes are structures which define the entity of cells and the organelles contained in them. In the membranes or in their proximities occur most of the biological processes and their lipids not only have a structural role, but also regulate the activity of important processes. Given that the lipid composition of the membrane depends to a great extent on ingested lipids, which then circulate through plasma until reaching the target cells, the intake of triglycerides rich in unsaturated or saturated very short chain fatty acids regulates the plasma lipid profile and the lipid composition of the membranes (Escribá et al., 2003). Thus, fat intake conditions in part the lipid content of the membranes and, as mentioned before, this has implications on cell function and, for this reason, on health. For example, regulation of the lipid composition of the membrane also influences the localisation or the function of important proteins involved in the control of cell physiology, such as G or PKC proteins (Escribá et al., 1995; 1997; Yang et al; 2005; Martinez et al., 2005). These and other studies demonstrate the importance lipids have on the control of important cell functions. In fact, numerous diseases in humans, such as, among others, cancer, cardiovascular pathologies, neurodegenerative processes, obesity, metabolic disorders, inflammation, infectious diseases, and autoimmune diseases, have been related to alterations in the levels or in the composition of the lipids present in the biological membranes, evidencing, moreover, the beneficial effects presented by treatments with other fatty acids which regulate the composition and structure of the membrane lipids, which can be used to reverse said diseases (Escribá, 2006).

Different studies carried out during the last few years indicate that membrane lipids play a much more important role than they had been assigned until now (Escribá et al., 2008). One example of said importance involves fish which live in rivers with a variable temperature, whose lipids experience significant changes (changes in composition and types of membrane lipids) when the temperature drops from 20° C. (summer) to 4° C. (winter) (Buda et al. 1994). These studies demonstrate that the changes in membrane lipids give rise to a series of modifications in the cell functions in a coordinated fashion to correctly maintain the cell functions, irrespective of external factors or pathophysiological processes. In the case of fish living in variable temperature waters, membrane lipid regulation allows their functions to be maintained in cell types of a very diverse nature. For this reason, it could be said that membrane lipids can determine the good or bad functioning of multiple signalling mechanisms and other cell functions in a wide variety of cells of different organs and tissues of the same animal.

Thus, alterations in the composition and structure of membranes are related to the aetiology of numerous pathologies and, in many cases, the manifestation of a determined disease is due to the combination of these alterations with others which affect determined proteins which interact with the membrane or which are found in the sequence of signals of other proteins that interact with them.

Therefore, one contribution of the present invention is to provide a compound that can regulate the composition of the membrane or plasma lipid profile and also for the permanence of said regulated composition or said plasma lipid profile to be more extended. Also, another contribution of the present invention consists of providing a compound that can modify certain cell functions effectively and safely with the net result of preventing the appearance of a determined pathological process (or several pathological processes) and/or to reverse them once they have appeared on the basis of its effect on cell membranes. Another contribution of the present invention consists of providing a compound for the prevention and/or treatment of diseases whose common aetiology is based on alterations of the plasma lipid profile (alterations in the circulating levels of lipids, the lipid metabolism, or composition), as well as of the structure and/or function of the lipids located in the cell membrane or with an altered regulation of cell signalling as a consequence of said alterations in said lipids present in the cell membrane. Specifically, one problem resolved by the present invention consists of providing compounds for the prevention and treatment of cardiovascular/metabolic diseases (e.g., high blood pressure, atherosclerosis, arteriosclerosis, heart attacks, ictus, arrhythmias, hypertriglyceridemia, hypercholesterolemia and other dyslipidaemias, obesity, diabetes, metabolic syndrome, etc.), cancer (lung cancer, breast cancer, prostate cancer, leukaemia, gliomas and other brain tumours pancreatic cancer, liver cancer, mesotheliomas, male and female gonadal tumours, head and neck cancer, kidney tumours, melanoma, etc.), and neurological/inflammatory diseases (Alzheimer's disease, Parkinson's disease, Huntington's disease, amyotrophic lateral sclerosis, multiple sclerosis, spinal injury, adult polyglucosan body disease (APBD), depression, anxiety, insomnia, pain, schizophrenia, general inflammation, local inflammation, including uveitis, rheumatism, inflammatory processes derived from arthritis, arthrosis, aging, etc.).

BRIEF DESCRIPTION OF THE INVENTION

The present invention relates to a compound of Formula I:

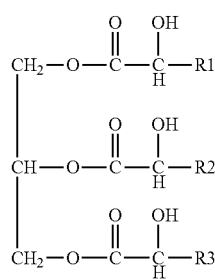

wherein R1, R2 and R3 are hydrocarbon moieties which comprise, each and independently, an aliphatic chain which comprises between 5 and 22 carbon atoms and between 0 and 6 double bonds, wherein said compound is selected from all the enantiomers, diastereoisomers, mesomeric compounds and the E/Z isomers possible from Formula I.

The present invention also relates to a method for producing a compound of Formula I, such as the one disclosed herein, wherein said method comprises three main steps:

A) formation of a 2-hydroxy-protected fatty acid of the Formula III

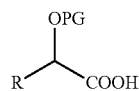

wherein R is a hydrocarbon moiety which comprises an aliphatic chain comprising between 5 and 22 carbon atoms and between 0 and 6 double bonds, and PG is an alcohol protecting group, from a 2-hydroxy fatty acid or the sodium salt of a 2-hydroxy fatty acid;

B) formation of the triglyceride of the Formula IV

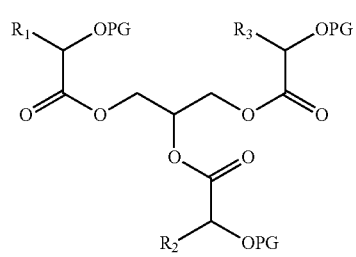

wherein R1, R2 and R3 are hydrocarbon moieties which comprise, each and independently, an aliphatic chain comprising between 5 and 22 carbon atoms and between 0 and 6 double bonds, and PG is defined as previously, by reaction of glycerol and at least one 2-hydroxy-protected fatty acid of the Formula III; and C) deprotection of the triglyceride of the Formula IV.

In addition, the present invention relates to a compound of the Formula I, described herein, to be used in the prevention and/or the treatment of at least one disease selected from among: cancer, metabolic/cardiovascular diseases, and/or neurological/inflammatory diseases. Similarly, the present invention relates to the use of at least one compound of the Formula I, like those disclosed herein, independently or in combination with at least one other compound, for the preparation of a medicament for use in the prevention and/or the treatment of at least one disease selected from among: cancer, metabolic/cardiovascular diseases, and/or neurological/inflammatory diseases.

Additionally, the present invention relates to a pharmaceutical and/or nutraceutical composition which comprises
a) at least one compound of the Formula I, like that disclosed in the present document; and
b) at least one excipient. Likewise, the present invention also relates to a method for preparing said pharmaceutical and/or nutraceutical composition, which comprises mixing at least one compound of the Formula I, like that disclosed in the present document, and at least one excipient.

In addition, the present invention relates to a method for the prevention and/or treatment of at least one disease in humans and animals which comprises administration to the patient of a therapeutically effective quantity of at least one compound of the Formula I, like that disclosed herein, or at least one pharmaceutical and/or nutraceutical composition also like that disclosed in the present document.

One last embodiment of the invention is a method for the prevention and/or treatment of a patient with at least one disease selected from among: cancer, metabolic/cardiovascular diseases, and/or neurological/inflammatory diseases, wherein at least one disease is selected from:
a) a cancer selected, in turn, from: lung cancer, breast cancer, prostate cancer, leukaemias, gliomas, pancreatic cancer, liver cancer, cervical cancer and/or neuroendocrine cancer;
b) a metabolic/cardiovascular disease selected, in turn, from: high blood pressure, hypertriglyceridemia, hypercholesterolemia, obesity and/or diabetes; and/or
c) a neurological/inflammatory disease selected, in turn, from: Alzheimer's disease and/or adult polyglucosan body disease,
comprising the administration to said patient of a therapeutically effective quantity or dose of at least one compound of the Formula I:

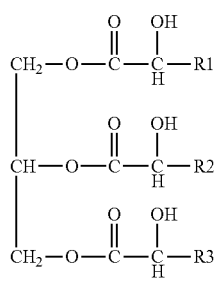

or at least one pharmaceutical and/or nutraceutical composition which comprises at least one compound of the Formula I, wherein R1, R2 and R3 are hydrocarbon moieties which comprise, each and independently, an aliphatic chain comprising between 5 and 22 carbon atoms and between 0 and 6 double bonds, preferably wherein R1, R2 and R3 are chosen from —$(CH_2)_4$—$CH_3$ [TGM0], —$(CH_2)_6$—(CH=CH—$CH_2)_1$—$(CH_2)_6$—$CH_3$ [TGM1], —$(CH_2)_6$—(CH=CH—$CH_2)_2$—$(CH_2)_3$—$CH_3$ [TGM2], —$(CH_2)_6$—(CH=CH—$CH_2)_3$—$CH_3$ [TGM3A], —$(CH_2)_3$—(CH=CH—$CH_2)_3$—$(CH_2)_3$—$CH_3$ [TGM3G], —$(CH_2)_2$—(CH=CH—$CH_2)_3$—$(CH_2)_3$—$CH_3$ [TGM4], —$(CH_2)_2$—(CH=CH—$CH_2)_5$—$CH_3$ [TGM5], and —$CH_2$—(CH=CH—$CH_2)_6$—$CH_3$ [TGM6] and R1=R2=R3.

Figure 1:
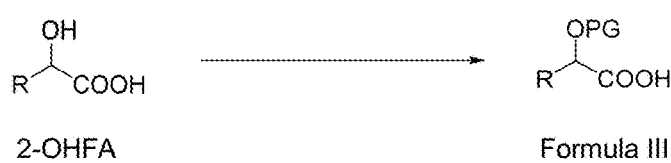
FIG. 1. General method of synthesis of the hydroxy-triglycerides defined in Table 1): A. Esterification of a 2-hydroxy fatty acid (2-OHFA), protection of the OH and hydrolysis of the ester to obtain fatty acid derivative, Formula III, wherein R, R1, R2 and R3 are hydrocarbon moieties which comprise, each and independently, an aliphatic chain comprising between 5 and 22 carbon atoms and between 0 and 6 double bonds (as defined herein) and OPG comprises an oxygen atom (O) which binds with (i) the carbon alpha to the carboxylic acid moiety of the fatty acid, and (ii) an alcohol protecting group (PG), wherein OPG is preferably defined as described herein; B. Reaction of the fatty acid derivative of Formula III, with glycerol to render the corresponding triglyceride, Formula IV; C. Deprotection of the triglyceride of Formula IV to obtain the triglyceride of the 2-hydroxy fatty acid (Formula I).
Figure 1:
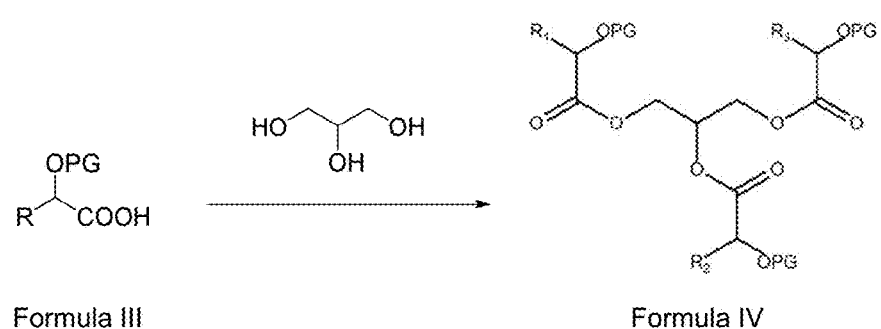
Figure 1:
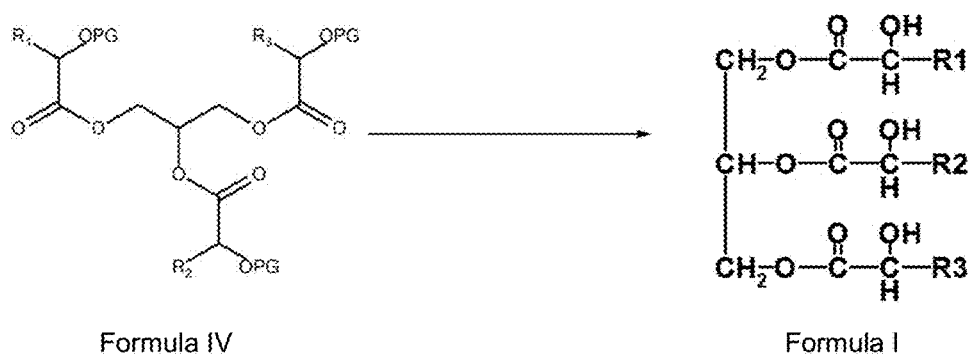

triglyceride caused by the lipoprotein lipase on the two compounds (expressed as a certain percentage) over time in minutes (X axis).

DETAILED DESCRIPTION OF THE INVENTION

The present invention centres on new molecular entities, hydroxy-triglycerides. The hydroxy-triglycerides of the present invention (which we also call TGM, from triglyceride mimetic, of the invention) are compounds of the Formula I:

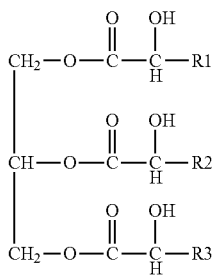

Formula I wherein R1, R2 and R3 are hydrocarbon moieties. Said hydrocarbon moieties comprise, each and independently, an aliphatic chain. Said aliphatic chain comprises between 5 and 22 carbon atoms and between 0 and 6 double bonds. Thus, each one of R1, R2 and R3 can be the same or a different hydrocarbon moiety which consists of a hydrocarbon chain of 5 to 22 carbon atoms and with 0 to 6 double bonds.

In a preferred embodiment of the compound of Formula I of the present invention, said hydrocarbon moieties R1, R2 and R3 comprise, each and independently, an aliphatic chain of between 5 and 22 carbon atoms of the Formula II:

$$-(CH_2)_a-(CH=CH-CH_2)_b-(CH_2)_c-CH_3 \qquad \text{Formula II}$$

wherein
a is a whole number between 1 and 6;
b is a whole number between 0 and 6; and
c is a whole number between 0 and 6.

In another preferred embodiment of the compound of Formula I of the present invention, R1, R2 and R3 are hydrocarbon moieties wherein each and independently are constituted by an aliphatic chain which comprises between 5 and 20 carbon atoms, or between 10 and 22 carbon atoms, more preferably between 12 and 20 carbon atoms, and even more preferably between 6 and 20 carbon atoms.

Likewise, in another preferred embodiment of the compound of Formula I of the present invention, said hydrocarbon moieties R1, R2 and R3 comprise, each and independently, an aliphatic chain of the Formula II, wherein a is a whole number between 1 and 6, b is a whole number between 1 and 6, and c is a whole number chosen from 0, 3 and 6; more preferably wherein a is a whole number between 1 and 6, b is a whole number between 2 and 6, and c is a whole number chosen from 0, 3 and 6; even more preferably wherein a is a whole number between 1 and 6, b is a whole number between 2 and 6, and c is a whole number chosen from 0 and 3. In another embodiment of the compound of Formula I of the present invention, said hydrocarbon moieties R1, R2 and R3 comprise, each and independently, an aliphatic chain of the Formula II, wherein a is a whole number chosen from 1 and 2, b is a whole number between 4 and 6, and c is a whole number chosen from 0 and 3.

Thus, in one preferred embodiment, the present invention relates to a compound of Formula I, wherein R1, R2 and R3 are hydrocarbon moieties, wherein said hydrocarbon moieties consist of, each and independently, an aliphatic chain of between 12 and 22 carbon atoms of the Formula II, wherein
a is a whole number between 1 and 6;
b is a whole number between 1 and 6; and
c is a whole number chosen from 0, 3 and 6.

In another preferred embodiment, the present invention relates to a compound of Formula I, wherein R1, R2 and R3 are hydrocarbon moieties, wherein said hydrocarbon moieties consist of, each and independently, an aliphatic chain of between 16 and 20 carbon atoms of the Formula II, wherein
a is a whole number between 1 and 6;
b is a whole number between 1 and 6; and
c is a whole number chosen from 0 and 3.

In another preferred embodiment, the present invention relates to a compound of Formula I, wherein R1, R2 and R3 are hydrocarbon moieties, wherein said hydrocarbon moieties consist of, each and independently, an aliphatic chain of between 16 and 20 carbon atoms of the Formula II, wherein
a is a whole number between 1 and 2;
b is a whole number between 4 and 6; and
c is a whole number chosen from 0 and 3.

In another preferred embodiment of the compound of Formula I of the present invention R1, R2 and R3 are chosen, each and independently, from $(CH_2)_4-CH_3$, $(CH_2)_6-(CH=CH-CH_2)_1-(CH_2)_6-CH_3$, $(CH_2)_6-(CH=CH-CH_2)_2-(CH_2)_3-CH_3$, $(CH_2)_6-(CH=CH-CH_2)_3-CH_3$, $(CH_2)_3-(CH=CH-CH_2)_3-(CH_2)_3-CH_3$, $(CH_2)_2-(CH=CH-CH_2)_4-(CH_2)_3-CH_3$, $(CH_2)_2-(CH=CH-CH_2)_5-CH_3$, and $CH_2-(CH=CH-CH_2)_6-CH_3$, more preferably from $(CH_2)_6-(CH=CH-CH_2)_2-(CH_2)_3-CH_3$, $(CH_2)_6-(CH=CH-CH_2)_3-CH_3$, $(CH_2)_3-(CH=CH-CH_2)_3-(CH_2)_3-CH_3$, $(CH_2)_2-(CH-CH-CH_2)_4-(CH_2)_3-CH_3$, $(CH_2)_2-(CH=CH-CH_2)_5-CH_3$, and $CH_2-(CH=CH-CH_2)_6-CH_3$.

The present invention catalogues different TGMs of the Formula I described on the basis of the number of double bonds of the acyl moiety. Thus, when all the hydrocarbon moieties R1, R2 and R3 have the same number of double bonds, the TGM is referred to as TGMX, wherein X represents the number of double bonds of the acyl moiety. In this sense, one TGM with all the hydrocarbon moieties R1, R2 and R3 without double bonds would be a TGM0, with 1 double bond in all the hydrocarbon moieties would be a TGM1, with two double bonds in all the hydrocarbon moieties would be a TGM2 and so on. Also, the combinations of hydrocarbon moieties with different numbers of double bonds could be represented using two or three numbers to refer to the number and type (but not the position) of the different chains that the TGM can have. For example, a TGM having two acyl moieties with 1 double bond and one acyl moiety with 4 double bonds would be a TGM114. Similarly, a TGM having one acyl moiety with 1 double bond, another acyl with 4 double bonds and a third hydrocarbon moiety with 6 double bonds, would be a TGM146. The number of each chain is proportional to the stoichiometry, specifically to the proportion, of each 2-hydroxy fatty acid used in the synthesis method. In this way, given that this nomenclature does not provide information in relation to the position (R1, R2, R3) of each chain, TGM114 also encompasses TGM141 and TGM411. In the event that the TGM should have only 2 different acyl moieties and its stoichiometry should be 1:1, the TGM would be symbolised with 2 numbers in the form TGMXY, wherein X and Y represent the number of double bonds of each acyl moiety (e.g., TGM12). Similarly, when the hydrocarbon moieties R1, R2 and R3 have a stoichiometry of 1:1:1 and at least one of the acyl moieties is different from the others, the TGM is referred to in form TGMXYZ, where X, Y and Z represent the number of double bonds of each acyl moiety. In this sense, it must be pointed out that the radicals R1, R2 and R3 can be constituted by the same or different hydrocarbon molecule of between 5 and 22 carbon atoms and between 0 and 6 double bonds and that given the molecule's capacity to rotate in the membrane it is irrelevant whether a hydrocarbon moiety is in one position (e.g., R1) or another (e.g., R3).

In a particular embodiment of the invention, the radicals R1, R2 and R3 can be substituted for the hydrocarbon moieties listed in table 1. Thus, in this preferred embodiment of the compound of Formula I of the present invention R1=R2=R3, wherein R1, R2 and R3 are chosen between —(CH$_2$)$_4$—CH$_3$ [1,2,3-tri(2'-hydroxyheptanoyl)glycerol, TGM0], —(CH$_2$)$_6$—(CH=CH—CH$_2$)$_1$—(CH$_2$)$_6$—CH$_3$ [1,2,3-tri(2'-hydroxy-octadec-9'-enoyl)glycerol, TGM1], —(CH$_2$)$_6$—(CH=CH—CH$_2$)$_2$—(CH$_2$)$_3$—CH$_3$[1,2,3-tri(2'-hydroxy-octadec-9',12'-dienoyl)glycerol, TGM2], —(CH$_2$)$_6$—(CH=CH—CH$_2$)$_3$—CH$_3$ [1,2,3-tri(2'-hydroxy-octadec-9',12',15'-trienoyl)glycerol, TGM3A], —(CH$_2$)$_3$—(CH=CH—CH$_2$)$_3$—(CH$_2$)$_3$—CH$_3$ [1,2,3-tri(2'-hydroxy-octadec-6',9',12'-trienoyl)glycerol, TGM3G], —(CH$_2$)$_2$—(CH=CH—CH$_2$)$_4$—(CH$_2$)$_3$—CH$_3$ [1,2,3-tri(2'-hydroxy-eicosa-5',8',11',14'-tetraenoyl)glycerol, TGM4], —(CH$_2$)$_2$—(CH=CH—CH$_2$)$_5$—CH$_3$ [1,2,3-tri(2'-hydroxy-eicosa-5',8',11',14',17'-pentaenoyl)glycerol, TGM5], and —CH$_2$—(CH=CH—CH$_2$)$_6$—CH$_3$ [1,2,3-tri(2'-hydroxy-docosa-4',7',10',13',16',19'-hexaenoyl)glycerol, TGM6]. Thus, in this embodiment, the compound of formula I of the present invention has hydrocarbon moieties R1, R2 and R3 chosen from compounds of formula II, wherein a is 4, b is 0 and c is 0 (TGM0), a is 6, b is 1 and c is 6 (TGM1), a is 6, b is 2 and c is 3 (TGM2), a is 6, b is 3 and c is 0 (TGM3A), a is 3, b is 3 and c is 3 (TGM3G), a is 2, b is 4 and c is 3 (TGM4), a is 2, b is 5 and c is 0 (TGM5), a is 1, b is 6 and c is 0 (TGM6). In one preferred embodiment of the compound of Formula I of the present invention R1=R2=R3, wherein R1, R2 and R3 are chosen preferably between —(CH$_2$)$_6$—(CH=CH—CH$_2$)$_1$—(CH$_2$)$_6$—CH$_3$ [TGM1], —(CH$_2$)$_6$—(CH=CH—CH$_2$)$_2$—(CH$_2$)$_3$—CH$_3$ [TGM2], —(CH$_2$)$_6$—(CH=CH—CH$_2$)$_3$—CH$_3$ [TGM3A], —(CH$_2$)$_3$—(CH=CH—CH$_2$)$_3$—(CH$_2$)$_3$—CH$_3$ [TGM3G], —(CH$_2$)$_2$—(CH=CH—CH$_2$)$_4$—(CH$_2$)$_3$—CH$_3$ [TGM4], —(CH$_2$)$_2$—(CH=CH—CH$_2$)$_5$—CH$_3$ [TGM5], and —CH$_2$—(CH=CH—CH$_2$)$_6$—CH$_3$ [TGM6] or from —(CH$_2$)$_6$—(CH=CH—CH$_2$)$_2$—(CH$_2$)$_3$—CH$_3$ [TGM2], —(CH$_2$)$_6$—(CH=CH—CH$_2$)$_2$—CH$_3$ [TGM3A], —(CH$_2$)$_3$—(CH=CH—CH$_2$)$_3$—(CH$_2$)$_3$—CH$_3$ [TGM3G], —(CH$_2$)$_2$—(CH=CH—CH$_2$)$_4$—(CH$_2$)$_3$—CH$_3$ [TGM4], —(CH$_2$)$_2$—(CH=CH—CH$_2$)$_5$—CH$_3$[TGM5], and —CH$_2$—(CH=CH—CH$_2$)$_6$—CH$_3$ [TGM6].

TABLE 1

Hydrocarbon moieties of compounds of Formula I used in therapy.

| Name | Double bonds | Series | Structure (R1, R2 and R3) |
|---|---|---|---|
| TGM0 | 0 | — | —(CH$_2$)$_4$—(CH=CH—CH$_2$)$_0$—(CH$_2$)$_0$—CH$_3$ |
| TGM1 | 1 | ω-9 | —(CH$_2$)$_6$—(CH=CH—CH$_2$)$_1$—(CH$_2$)$_6$—CH$_3$ |
| TGM2 | 2 | ω-6 | —(CH$_2$)$_6$—(CH=CH—CH$_2$)$_2$—(CH$_2$)$_3$—CH$_3$ |
| TGM3A | 3 | ω-3 | —(CH$_2$)$_6$—(CH=CH—CH$_2$)$_3$—(CH$_2$)$_0$—CH$_3$ |
| TGM3G | 3 | ω-6 | —(CH$_2$)$_3$—(CH=CH—CH$_2$)$_3$—(CH$_2$)$_3$—CH$_3$ |
| TGM4 | 4 | ω-6 | —(CH$_2$)$_2$—(CH=CH—CH$_2$)$_4$—(CH$_2$)$_3$—CH$_3$ |
| TGM5 | 5 | ω-3 | —(CH$_2$)$_2$—(CH=CH—CH$_2$)$_5$—(CH$_2$)$_0$—CH$_3$ |
| TGM6 | 6 | ω-3 | —(CH$_2$)$_1$—(CH=CH—CH$_2$)$_6$—(CH$_2$)$_0$—CH$_3$ |

By way of an example, and taking the complete structure of one of the molecules of the present invention, TGM1 would be characterised by substituting for R1, R2 and R3 the molecule indicated in Table 1 on the Formula I, shown above. The complete structure of the TGM1 would, therefore, be the following:

TGM1

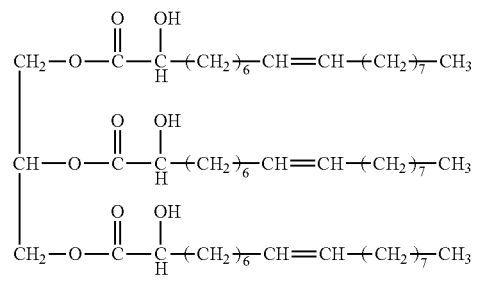

Also, the compound of Formula I of the present invention comprises all the stereoisomers of said compound. In other words, the compound of the present invention comprises all the isomers which have the same molecular formula and same sequence of bonded atoms, with the same bonds between their atoms, as that of Formula I, but which differ in the three-dimensional orientation of their atoms in space, due to the fact that said compound comprises a stereocenter at each one of the three carbons to which a hydroxyl is bonded, and optionally at least one double bond. Thus, the compound of Formula I of the present invention comprises also all the enantiomers, diastereoisomers, mesomeric compounds and E/Z isomers possible on the basis of Formula I. Preferably, in a sample of the compound of the present invention, each one of the three hydroxy-acyl moieties which each compound of the present invention has, could likewise be isomers (R) and (S).

The present invention also relates to a method for the production (method of synthesis) of a compound of Formula I, like the general method described above (cf. FIG. 1). Said method comprises three main steps, as follows: A) formation of a 2-hydroxy-protected fatty acid of the Formula III

III

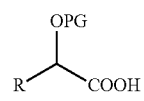

wherein R is a hydrocarbon moiety which comprises an aliphatic chain comprising between 5 and 22 carbon atoms and between 0 and 6 double bonds, and PG is an alcohol protecting group, from a 2-hydroxy fatty acid or the sodium salt of a 2-hydroxy fatty acid (cf. FIG. 1A); B) formation of the triglyceride of Formula IV

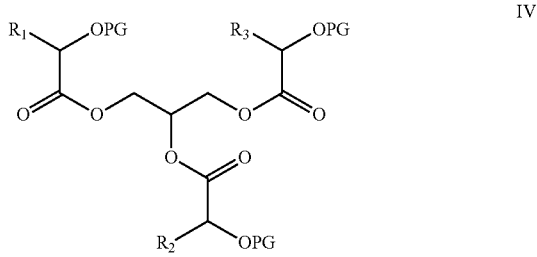

wherein R1, R2 and R3 are hydrocarbon moieties which comprise, each and independently, an aliphatic chain comprising between 5 and 22 carbon atoms and between 0 and 6 double bonds, and PG is defined as above, by reaction of glycerol and at least one 2-hydroxy-protected fatty acid of Formula III (cf. FIG. 1B); and C) deprotection of the triglyceride of Formula IV (cf. FIG. 1C). In one preferred embodiment OPG comprises an oxygen atom (O) which is bonded with (i) the alpha carbon to the carboxylic acid moiety of the fatty acid, and (ii) an alcohol protecting group (PG), wherein preferably OPG is selected from a silyl ether moiety, an alkyl ether moiety, an alkoxy methyl ether moiety, a methylthiomethyl ether moiety, an alkyl ester moiety, a methoxyalkyl ester moiety, a haloalkyl ester moiety, a benzyl ester moiety, an oxoalkyl ester moiety, a carbonic ester moiety or an acetal moiety. Step A) comprises optionally a first step i) formation of the 2-hydroxy fatty acid from the sodium salt of a 2-hydroxy fatty acid and three following steps ii) esterification of the acid moiety of the 2-hydroxy fatty acid, preferably with an alcohol, to obtain the corresponding ester of the 2-hydroxy fatty acid; iii) protection of the hydroxyl moiety in position 2 of the 2-hydroxy fatty acid ester to obtain an ester of the 2-OPG fatty acid; and iv) hydrolysis of the ester of the 2-OPG fatty acid to obtain the 2-OPG fatty acid, wherein the OPG comprises one oxygen atom (O) which is bonded with (i) the carbon alpha to the carboxylic acid moiety, or to the ester moiety of the carboxylic acid, of the fatty acid, and (ii) one alcohol protecting group (PG), wherein preferably OPG is selected from a silyl ether moiety, an alkyl ether moiety, an alkoxy methyl ether moiety, a methylthiomethyl ether moiety, an alkyl ester moiety, a methoxyalkyl ester moiety, a haloalkyl ester moiety, a benzyl ester moiety, an oxoalkyl ester moiety, a carbonic ester moiety or an acetal moiety. Alternatively, step A) comprises reaction of the alpha carbon of a fatty acid or the sodium salt of a fatty acid to obtain a 2-OPG fatty acid. As another alternative, step A) comprises optionally a first step i) formation of the fatty acid from the sodium salt of a fatty acid and three following steps ii) esterification of the acid moiety of the fatty acid to obtain the corresponding ester of the fatty acid; iii) reaction of the alpha carbon of the fatty acid ester to obtain an ester of the 2-OPG fatty acid; and iv) hydrolysis of the ester of the 2-OPG fatty acid to obtain the 2-OPG fatty acid, wherein step iii) optionally comprises a) hydrolysis of the 2-OPG moiety of the ester of the 2-OPG fatty acid to obtain an ester of the 2-hydroxy fatty acid and b) protection of the hydroxyl moiety in position 2 of the ester of the 2-hydroxy fatty acid to obtain another ester of the 2-OPG fatty acid. As another alternative, step A) comprises optionally a first step i) formation of the fatty acid from the sodium salt of a fatty acid and four following steps ii) esterification of the acid moiety of the fatty acid to obtain the corresponding ester of the fatty acid; iii) hydroxylation of the alpha carbon of the fatty acid ester to obtain an ester of the 2-hydroxy fatty acid; iv) protection of the hydroxyl moiety in position 2 of the ester of the 2-hydroxy fatty acid to obtain an ester of the 2-OPG fatty acid; and v) hydrolysis of the ester of the 2-OPG fatty acid to obtain the 2-OPG fatty acid, wherein the OPG moiety is defined as has been mentioned above.

In an alternative embodiment of the method for the production (method of synthesis) of a compound of Formula I, said method comprises optionally a first step i) formation of the fatty acid from the sodium salt of a fatty acid and three following steps A1) formation of a tri(acyl)glycerol by reaction of glycerol and said fatty acid; B2) reaction of the alpha carbon of each moiety of the fatty acid to obtain a tri(2-hydroxy-protected acyl)glycerol; and C) deprotection to obtain the tri(2-hydroxy-acyl)glycerol (cf. FIG. 1C). In one preferred embodiment, said method comprises optionally a first step i) formation of the fatty acid from the sodium salt of a fatty acid and three following steps A2) formation of a tri(acyl)glycerol by reaction of glycerol and said fatty acid; B2) hydroxylation of the alpha carbon of each moiety of the fatty acid to obtain the tri(2-hydroxy-acyl)glycerol. In said embodiments, steps A1) and A2) preferably comprise reaction of glycerol and at least one type and up to three types of 2-hydroxy-protected fatty acid.

In the present invention moreover it is proven how the hydroxy-triglycerides can be used with success to prevent the appearance of certain diseases or to reverse them, once they have appeared. Specifically, the present invention relates to a compound of the Formula I, according to that described above, to be used as a food and/or medicine, preferably in the treatment and/or prevention of at least one disease or pathology united by their aetiology, relative to alterations of the plasma lipid profile or the structure or function of the membrane lipids. Said disease or pathology, united by said common aetiology, and prevented or treated by means of the use of hydroxy-triglycerides of the invention is a cancer, a metabolic/cardiovascular disease, and/or a neurological/inflammatory disease.

Thus, the present invention relates to a compound of Formula I, according to that described above, to be used in the prevention and/or the treatment of at least one disease chosen from among: cancer, metabolic/cardiovascular diseases, and/or neurological/inflammatory diseases. Similarly, the present invention also relates to the use of at least one compound of Formula I, according to that described above, independently or in combination with at least one other compound, for the preparation of a medicine to be used in the prevention and/or the treatment of at least one disease chosen from among: cancer, metabolic/cardiovascular diseases, and/or neurological/inflammatory diseases. Said use of at least one compound of Formula I, can be independent or in combination with at least one other compound.

Said diseases or pathologies, united by said common aetiology, and prevented or treated by means of the use of hydroxy-triglycerides of the invention are preferably, for example:

Cardiovascular/metabolic diseases: hypertension, atherosclerosis, arteriosclerosis, heart attacks, ictus, arrhythmias, hypertriglyceridemia, hypercholesterolemia and other dyslipidaemias, diabetes, obesity, metabolic syndrome, etc.

Cancer: Lung cancer, breast cancer, prostate cancer, leukaemia, gliomas and other brain tumours, pancreatic cancer, liver cancer, mesotheliomas, male and female gonadal tumours, head and neck cancer, kidney tumours, melanoma, etc.

Neurological/neurodegenerative diseases: Alzheimer's disease, Parkinson's disease, Huntington's disease, amyotrophic lateral sclerosis, multiple sclerosis, spinal injury, adult polyglucosan body disease (APBD), depression, anxiety, insomnia, pain, schizophrenia, general inflammation, local inflammation, including uveitis, rheumatism, inflammatory processes derived from arthritis, arthrosis, aging, etc.

Thus, in one preferred embodiment of the compound of the Formula I, described above, and/or the use of the compound of the Formula I, described above, the at least one disease is selected from:
a) a cancer selected, in turn, from: lung cancer, breast cancer, prostate cancer, leukaemias, gliomas and/or other brain tumours, pancreatic cancer, liver cancer, cervical cancer, neuroendocrine cancer, mesotheliomas, male and/or female gonadal tumours, head and/or neck cancer, kidney tumours and/or melanoma;
b) a metabolic/cardiovascular disease selected, in turn, from: hypertension, atherosclerosis, arteriosclerosis, heart attacks, ictus, arrhythmias, hypertriglyceridemia, hypercholesterolemia and/or other dyslipidaemias, obesity, diabetes, and/or metabolic syndrome; and/or
c) a neurological/inflammatory disease selected, in turn, from: Alzheimer's disease, Parkinson's disease, Huntington's disease, amyotrophic lateral sclerosis, multiple sclerosis, spinal injury, adult polyglucosan body disease, depression, anxiety, pain, schizophrenia, insomnia, general inflammation, and/or local inflammation, including uveitis, rheumatism, inflammatory processes derived from arthritis, arthrosis and/or aging.

In one embodiment of greater preference, of the compound of Formula I, described above, and/or of the use of the compound of Formula I, described above, at least one disease is selected from:
a) a cancer selected, in turn, from: lung cancer, breast cancer, prostate cancer, leukaemias, gliomas, pancreatic cancer, liver cancer, cervical cancer and/or neuroendocrine cancer;
b) a metabolic/cardiovascular disease selected, in turn, from: hypertension, hypertriglyceridemia, hypercholesterolemia, obesity and/or diabetes; and/or
c) a neurological/inflammatory disease selected, in turn, from: Alzheimer's disease and/or adult polyglucosan body disease.

Therefore, the present invention relates to a compound of Formula I with radicals R1, R2 and R3, which can be the same or different and which have hydrocarbon moieties with 5 to 22 carbon atoms and 0 to 6 double bonds, to be used, independently or in combination with other compounds, as a medicine in humans and animals for the prevention and treatment of cardiovascular diseases and obesity, cancer, neurodegenerative diseases, psychiatric disorders, and metabolic diseases.

At the same time, in one especially preferred embodiment, the present invention relates to a compound of Formula I, wherein R1, R2 and R3 are hydrocarbon moieties, wherein said hydrocarbon moieties consist of, each and independently, one aliphatic chain of between 16 and 22 carbon atoms of the Formula II, wherein
a is a whole number between 1 and 6;
b is a whole number between 1 and 6; and
c is a whole number chosen from 0, 3 and 6, to be used in the prevention and/or treatment of at least one disease, wherein said disease is selected from:
a) a cancer selected, in turn, from: lung cancer, breast cancer, prostate cancer, leukaemias, gliomas, pancreatic cancer, liver cancer, lung cancer, cervical cancer and/or neuroendocrine cancer;
b) a metabolic/cardiovascular disease selected, in turn, from: hypertension, hypertriglyceridemia, hypercholesterolemia, obesity and/or diabetes; and/or
c) a neurological/inflammatory disease selected, in turn, from: Alzheimer's disease and/or adult polyglucosan body disease.

The broad spectrum of therapeutic application which the hydroxy-triglycerides of the present invention offer makes it possible to assume in a generalised manner that these lipids confer specific structural properties to the membranes which allow for the correct activity of the processes carried out in and by said membranes in the cells. To put it differently, the hydroxy-triglycerides of the invention can be effectively used for the prevention and/or treatment of any disease whose aetiology is related either to alterations in the levels, the composition, the structure or of any other type of molecular or supramolecular characteristic, of the lipids of the biological membranes or with an altered regulation of the cell signalling as a consequence of said alterations in said lipids present in the biological membranes. Likewise, the effect of these hydroxy-triglycerides is related to the circulating levels of plasma lipids or the lipid metabolism. In summary, the hydroxy-triglycerides of the present invention are capable of regulating in a positive manner (preventing and/or curing) alterations related to body lipids.

The broad spectrum of therapeutic application which the hydroxy-triglycerides of the present invention offer (cf. Examples 2 to 4 and FIGS. 2 to 5 and 7) is justified by various phenomena. In the first place, the intake of oils and butters with natural triglycerides that can have positive or negative effects for health is manifested through multiple factors. For example, the intake of olive oil (rich in triglycerides with a high content in monounsaturated acyl moieties) has a positive repercussion on cardiovascular health (Escribá et al., 2003), protects against obesity (Peñalvo et al., 2012), against dyslipidaemias (Kimura et al., 2013), prevents the development of diabetes (Perona et al., 2007), reduces the incidence of cancer (Barone et al., 2014), etc. When a determined type of natural triglyceride (not hydroxylated) is ingested, the latter is distributed throughout the organism and gives rise to the regulation of the lipid species of the cell membranes of all the organs. For this reason, both certain natural oils and the hydroxy-triglycerides of the present invention penetrate in all cells and are integrated into the cell membranes (cf. FIG. 8) producing a positive effect on various types of pathologies.

Figure 8:
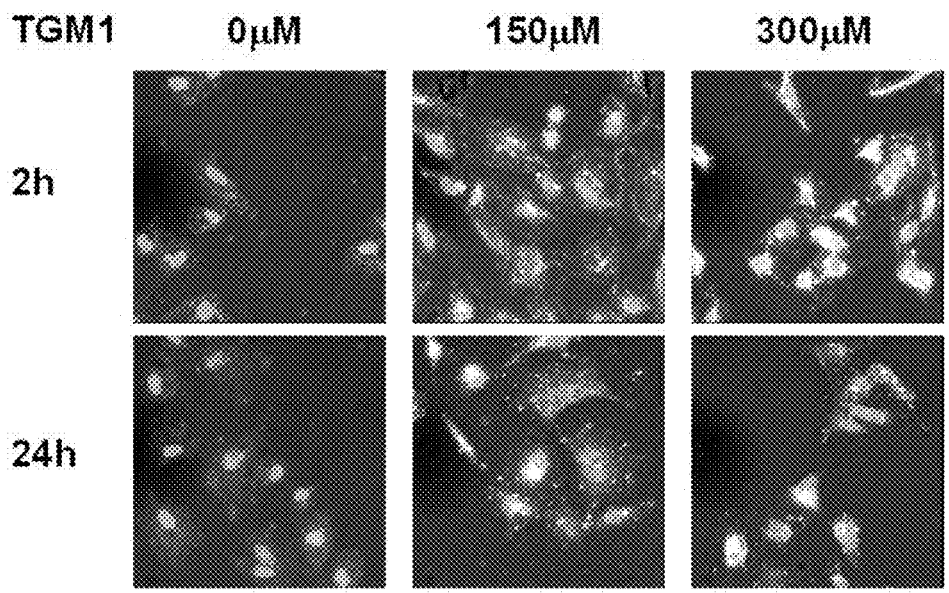
FIG. 8. Accumulation of TGM1 in intracellular vesicles and membranes. Concentrations of 0, 150 μM and 300 μM were used and penetration in the cell membranes was measured at 2 and 24 hours. The figure shows in colour blue the broad nuclear marking and in red small dots that show the location of the triglycerides. Marking with TGM1 in red nearer to the nucleus marked in blue (large central stain) corresponds to intracellular membranes and vesicles, whereas the red marking further away from the nucleus corresponds to the presence in plasma membranes.
Figure 9:
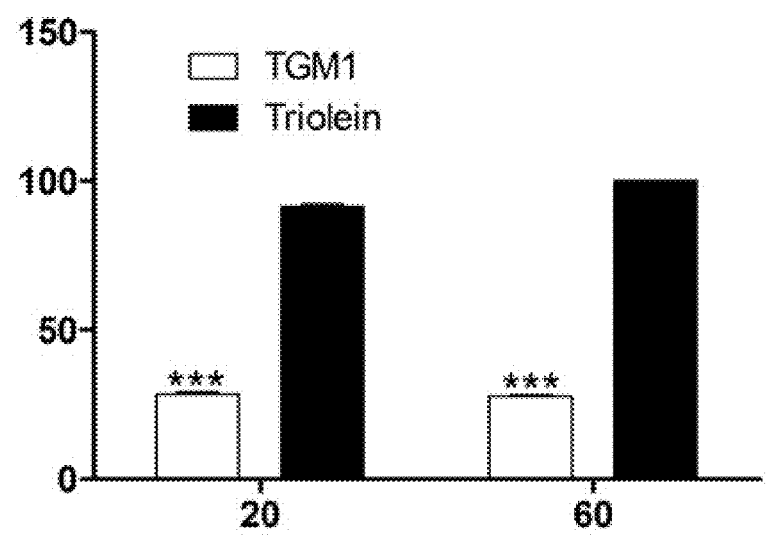
FIG. 9. Degradation of the natural triglyceride triolein and of the hydroxy-triglyceride TGM1. The figure shows the degradation of the natural (triolein) or synthetic (TGM1)

Secondly, the changes in the levels of lipids that are produced as a consequence of determined physiological or pathological processes (such as acclimatisation to cold water in poikilothermic fish) affect practically all of the organism's cells (Buda et al., 1994). This result indicates that there is a coordinated effect of the lipids in all the cells of the organism and that the modifications in lipids regulate all the cells in the same direction, whether with positive or negative effects. Finally, triglycerides can be stored or degraded to produce energy. In fact, these molecules constitute exceptional cell fuels, meaning that the direct use of non-modified oils has a modest impact on health. In this sense, various enzymes, such as lipoprotein lipase, are capable of metabolising triglycerides, liberating fatty acids which would be metabolised through the β-oxidation. However, the blocking of their degradation, through structural modifications such as those which appear in the present invention (hydroxylation), allow for permanence of these molecules in a prolonged manner, both in serum and in membranes, thus allowing for their therapeutic action (cf. FIGS. 8 and 9). Also, the acyl moieties which degradation (slow: FIG. 9) of the hydroxy-triglycerides of the present invention gives rise to, cannot be metabolised through β-oxidation, but through a much slower process, α-oxidation (Foulon et al., 2005). For this reason, the hydroxy-triglycerides used in the present invention produce a wide range of positive effects for health in general, and for the prevention and treatment of the pathologies indicated above, without observable secondary effects. Thus, the hydroxy-triglycerides of the present invention present modifications with respect to natural triglycerides to slow down their metabolism, increasing the time of their presence in the organism, and, through this, their therapeutic effect. It has been possible to confirm this slower metabolism in an experimental manner (FIG. 9).

The broad spectrum of therapeutic application offered by the hydroxy-triglycerides of the present invention allow it to be assumed in a generalised manner that these lipids give membranes specific structural properties which allow for the correct activity of the processes carried out in and by said membranes. In fact, the mechanism of action of these molecules (based on the regulation of the composition and structure of the biological membranes) is different to that of most of the drugs used to treat human pathologies (based on the interaction with proteins, in most cases, or nucleic acids). For this reason, they can be used in combination therapies in which one of the compounds of the present invention is used plus, at least, another molecule (active principle and/or excipient) which can turn out to be much more effective than monotherapy with just one of the compounds.

The hydroxy-triglycerides of the invention can be administered independently or formulated in pharmaceutical or nutraceutical compositions in which they are combined with excipients. Thus, the present invention relates to a pharmaceutical and/or nutraceutical composition, which comprises a) at least one compound of Formula I, according to any of claims 1 to 8; and b) at least one excipient. At the same time, the present invention relates to a method for the preparation of a pharmaceutical and/or nutraceutical composition, like the one described above, which comprises mixing a) at least one compound of Formula I, described above; and b) at least one excipient.

Said excipient can be selected from binders, fillers, disintegrators, lubricants, coaters, sweeteners, flavourings, colourings, carriers, antioxidants, compactors, stabilisers, etc. and combinations thereof. Likewise, the hydroxy-triglycerides of the invention can form part of pharmaceutical or nutraceutical compositions, in combination with other active principles. In one preferred embodiment, the pharmaceutical and/or nutraceutical composition of the present invention comprises at least two different compounds of Formula I, described herein. For the purposes of the present invention the term nutraceutical is defined as a compound which is ingested periodically during meals or as a complement thereto and which serves to prevent or reverse diseases, in this case, whose aetiology is linked to alterations in cell membrane lipids.

Finally, the present invention relates to a method for the prevention and/or therapeutic treatment of at least one disease in humans and animals whose common aetiology is related to structural and/or functional alterations of the lipids located in cell membranes or circulating in plasma, which comprises the administration to the patient of a therapeutically effective quantity of at least one compound of Formula I of the present invention, like the one described above. Additionally, the present invention relates to a method for the prevention and/or therapeutic treatment of at least one disease in humans and animals which comprises the administration to the patient of a therapeutically effective quantity of at least one compound of Formula I of the present invention, according to that described above, or at least one pharmaceutical and/or nutraceutical composition according to that described above. In one preferred embodiment of the method said at least one disease is selected from cancers, metabolic/cardiovascular pathologies, and/or neurological/inflammatory pathologies, more preferably said disease is selected from among:

a) a cancer selected, in turn, from: lung cancer, breast cancer, prostate cancer, leukaemias, gliomas and/or other brain tumours, pancreatic cancer, liver cancer, cervical cancer, neuroendocrine cancer, mesotheliomas, male and/or female gonadal tumours, head and/or neck cancer, kidney tumours and/or melanoma;

b) a metabolic/cardiovascular disease selected, in turn, from: hypertension, atherosclerosis, arteriosclerosis, heart attacks, ictus, arrhythmia, hypertriglyceridemia, hypercholesterolemia and/or other dyslipidaemias, obesity, diabetes, and/or metabolic syndrome; and/or c) a neurological/inflammatory disease selected, in turn, from: Alzheimer's disease, Parkinson's disease, Huntington's disease, amyotrophic lateral sclerosis, multiple sclerosis, spinal injury, adult polyglucosan body disease, depression, anxiety, pain, schizophrenia, insomnia, general inflammation, and/or local inflammation, including uveitis, rheumatism, inflammatory processes derived from arthritis, arthrosis and/or aging. In one even more preferable embodiment, said disease is selected from:

a) a cancer selected, in turn, from: lung cancer, breast cancer, prostate cancer, leukaemias, gliomas, pancreatic cancer, liver cancer, cervical cancer and/or neuroendocrine cancer;

b) a metabolic/cardiovascular disease selected, in turn, from: hypertension, hypertriglyceridemia, hypercholesterolemia, obesity and/or diabetes; and/or c) a neurological/inflammatory disease selected, in turn, from: Alzheimer's disease and/or adult polyglucosan body disease.

For the purposes of the present invention a "therapeutically effective quantity" is understood to mean that which reverses the disease or prevents it without showing adverse secondary effects or, which if it does produce them, are assumable on the basis of the criteria defined by the regulatory agencies in pharmaceutical matters (basically, that the benefit produced is greater than the damage caused; e.g. episodes of nausea would be assumable in a cancer patient with a serious prognosis).

The administration of the hydroxy-triglycerides of the invention can be carried out via any path, for example, enteral (through the digestive system), oral (through pills, capsules, granulates, emulsions, tablets or syrups), rectal (through suppositories or enemas), topical (through creams or patches), inhaled, parenteral injected, through IV injection, intramuscular injection or subcutaneous injection, in the form indicated above or any other type of pharmaceutically acceptable form, etc. The oils described in the present invention also have the capacity to be administered in oral, intraperitoneal, intravenous, subcutaneous or topical form, without apparent secondary effects at nutraceutical or pharmaceutical doses.

On a separate note, the composition comprised of a hydroxy-triglyceride of the invention and of another active principle is effective in the prevention and treatment of the indications cited above. In other words, in one preferred embodiment of the method for the prevention and/or therapeutic treatment of at least one disease in humans and animals which comprises the administration to the patient of a therapeutically effective quantity of at least one compound of Formula I or at least one pharmaceutical and/or nutraceutical composition according to that described above, said at least one disease is selected from cancers, metabolic/cardiovascular pathologies, and/or neurological/inflammatory pathologies. More preferably, said at least one disease is selected between:

a) a cancer selected, in turn, from: lung cancer, breast cancer, prostate cancer, leukaemias, gliomas and/or other brain tumours, pancreatic cancer, liver cancer, cervical cancer, neuroendocrine cancer, mesotheliomas, male and/or female gonadal tumours, head and/or neck cancer, kidney tumours and/or melanoma;
b) a metabolic/cardiovascular disease selected, in turn, from: hypertension, atherosclerosis, arteriosclerosis, heart attacks, ictus, arrhythmia, hypertriglyceridemia, hypercholesterolemia and/or other dyslipidaemias, obesity, diabetes, and/or metabolic syndrome; and/or
c) a neurological/inflammatory disease selected, in turn, from: Alzheimer's disease, Parkinson's disease, Huntington's disease, amyotrophic lateral sclerosis, multiple sclerosis, spinal injury, adult polyglucosan body disease, depression, anxiety, pain, schizophrenia, insomnia, general inflammation, and/or local inflammation, including uveitis, rheumatism, inflammatory processes derived from arthritis, arthrosis and/or aging.

In one indication of greater preference, said at least one disease is selected from:

a) a cancer selected, in turn, from: lung cancer, breast cancer, prostate cancer, leukaemias, gliomas, pancreatic cancer, liver cancer, cervical cancer and/or neuroendocrine cancer;
b) a metabolic/cardiovascular disease selected, in turn, from: hypertension, hypertriglyceridemia, hypercholesterolemia, obesity and/or diabetes; and/or
c) a neurological/inflammatory disease selected, in turn, from: Alzheimer's disease and/or adult polyglucosan body disease.

EXAMPLES

Example 1: Method of Synthesis of the 2-Hydroxy-Triglycerides Exemplified by the Formation of the 2-Hydroxy-Triglyceride TGM1

A) Formation of the 2-hydroxy-octadecanoic acid protected in the hydroxyl of the alpha carbon with a MOM protector group (acid 2-methoxymethyloxo-octadecanoic, Formula III in FIG. 1A, where R=the cis isomer of $-(CH_2)_6-CH=CH-(CH_2)_7-CH_3$ and OPG=$-OCH_2OCH_3$).

i) Formation of the Acid

The sodium salt of the 2 hydroxy-octadecanoic acid, methyl tert-butyl ether (MTBE) and hydrochloric acid 3M (HCl) are loaded into a reactor with mechanical agitation. It is agitated until obtaining a clear solution. Once the clear dissolution has been obtained, agitation is stopped and the phases are separated. The organic phase is vacuum concentrated (99% yield) to obtain crude 2-hydroxy-octadecanoic acid.

ii) Esterification

The crude 2-hydroxy-octadecanoic acid [2-OHFA in FIG. 1A, where R=the cis isomer of $-(CH_2)_6-CH=CH-(CH_2)_7-CH_3$] is dissolved in a solution of methanol (MeOH in sulphuric acid, $H_2SO_4$) and is heated to 60° C. The reaction is stopped by neutralising with sodium carbonate ($Na_2CO_3$). The crude product obtained is extracted with MTBE, vacuum concentrated and the methyl ester of 2-hydroxy-octadecanoic acid is obtained (96% yield).

iii) OH Protection

The methyl ester of 2 hydroxy-octadecanoic acid is loaded into the reactor and dissolved in toluene. Chloromethyl methyl ether (CMME) and p-toluenesulfonic acid (pTSA) are added to the dissolution. The reaction is agitated for 60 min and is neutralised with saturated sodium bicarbonate ($NaHCO_3$). The methyl ester of the 2-methoxymethyloxy-octadecanoic acid is obtained.

iv) Hydrolysis

The methyl ester of 2-methoxymethyloxy-octadecanoic acid is loaded in a reactor and is dissolved in tetrahydrofuran (THF). A solution of potassium hydroxide (KOH) in water is added to this solution. The solution is heated to 40° C. for 1 h. The reaction is stopped with HCl (3 M) and is extracted, afterwards the organic phase is vacuum concentrated. The 2-methoxymethyloxy-octadecanoic acid is obtained [Formula III in FIG. 1A, where R=the cis isomer of $-(CH_2)_6-CH=CH-(CH_2)_7-CH_3$ and OPG=$-OCH_2OCH_3$] (99% yield).

B. Formation of the tri(2-methoxymethyloxy-octadecenoyl)glycerol [Formula IV in FIG. 1B, where R=the cis isomer of $-(CH_2)_6-CH=CH-(CH_2)_7-CH_3$ and OPG=$-OCH_2OCH_3$].

In a reactor with a dropping funnel, thermometer and under an inert atmosphere (with $N_2$), 2-methoxymethyloxy-octadecanoic acid is added [Formula III in FIG. 1A, where R=the cis isomer of $-(CH_2)_6-CH=CH-(CH_2)_7-CH_3$ and OPG=$-OCH_2OCH_3$], glycerol and 4-dimethylaminopyridine (DMAP). It is all dissolved in dichloromethane ($CH_2Cl_2$) and cooled to 5° C. When the solution has cooled then the dropping funnel is used to add the solution of N,N'-dicyclohexylcarbodiimide (DCC) in $CH_2Cl_2$. The reaction is heated at reflux (40° C.) for 2-3 days. The reaction is filtered on a celite bed and the solid is washed with $CH_2Cl_2$. The filtered liquid is washed with saturated $NaHCO_3$, saturated $NH_4Cl$ and saturated NaCl. The organic phase is dried over magnesium sulphate ($MgSO_4$), is filtered and is vacuum concentrated. A crude product is obtained which contains about 69% of triglyceride tri(2-methoxymethyloxy-octadecenoyl)glycerol [Formula IV in FIG. 1B, were R=the cis isomer of $-(CH_2)_6-CH=CH-(CH_2)_7-CH_3$ and OPG=$-OCH_2OCH_3$]. The crude product is purified by flash chromatography on a column to obtain said compound in 90% purity.

C. Deprotection to obtain the tri(2-hydroxy-octadecenoyl)glycerol [Formula I in FIG. 1C, where R=the cis isomer of $-(CH_2)_6-CH=CH-(CH_2)_7-CH_3$]).

Triglyceride tri(2-methoxymethyloxy-octadecenoyl)glycerol [Formula IV in FIG. 1B, where R=the cis isomer of $-(CH_2)_6-CH=CH-(CH_2)_7-CH_3$ and OPG=$-OCH_2OCH_3$] is dissolved in acetone and water and pyridinium para-toluenesulfonate (ppts) is added. It is heated at reflux for 12 h. The reaction is stopped, evaporating the acetone and extracting with MTBE and $H_2O$. The organic phase is washed 3 times with water. The organic phase is dried on $MgSO_4$, filtered and vacuum concentrated. The hydroxy-triglyceride, tri(2-hydroxy-octadecenoyl)glycerol is obtained [Formula I in FIG. 1C, where R=the cis isomer of $-(CH_2)_6-CH=CH-(CH_2)_7-CH_3$, =TGM1, see Table 1] (90% purity). The total yield of the process was 70%.

The same procedure was used with the sodium salts of the other 2 hydroxy-fatty acids which comprise the other acyl radicals listed above to obtain the different TGMs listed in Table 1.

Example 2. Use of the Hydroxy-Triglycerides of the Invention in the Prevention and/or Treatment of Cancer To study whether the hydroxy-triglycerides of the present invention have applications in the prevention and treatment of tumour processes, two models were used: in vitro and in vivo.

A) In Vitro Model

Figure 2:
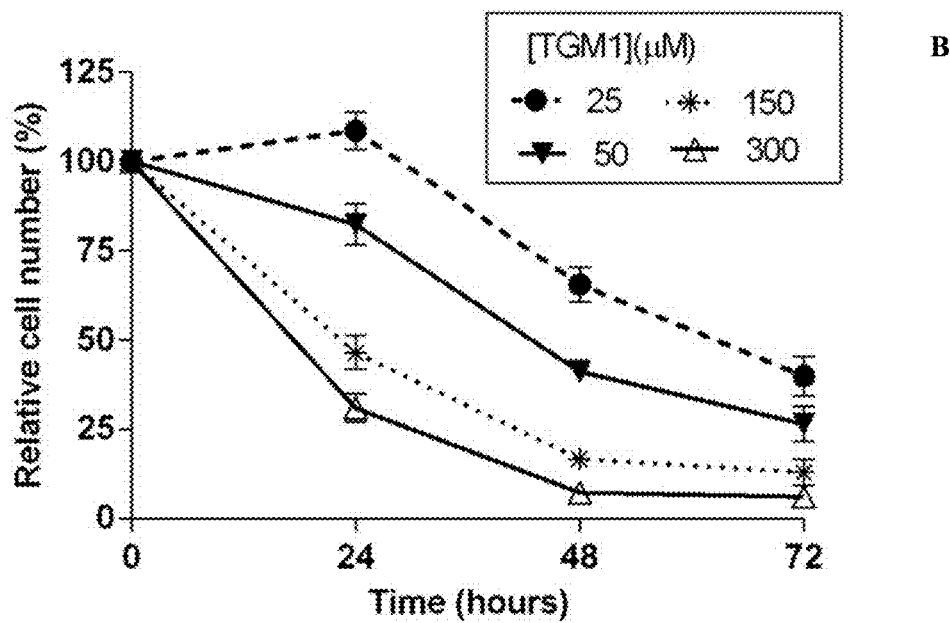
FIG. 2. Antitumor efficacy of the hydroxy-triglycerides A. TGM1; B. TGM2; C. TGM4; and D. TGM6 against the proliferation of human lung cancer (A549) cells in vitro: shows the inhibition of tumour cell growth produced by molecules TGM1, TGM2, TGM4 and TGM6 as a function of concentration (shown in the boxes) and incubation time (0 to 72 hours). The number of cells appears on the ordinate (Y) axis expressed as a % of the number of cells without treatment.
Figure 2:
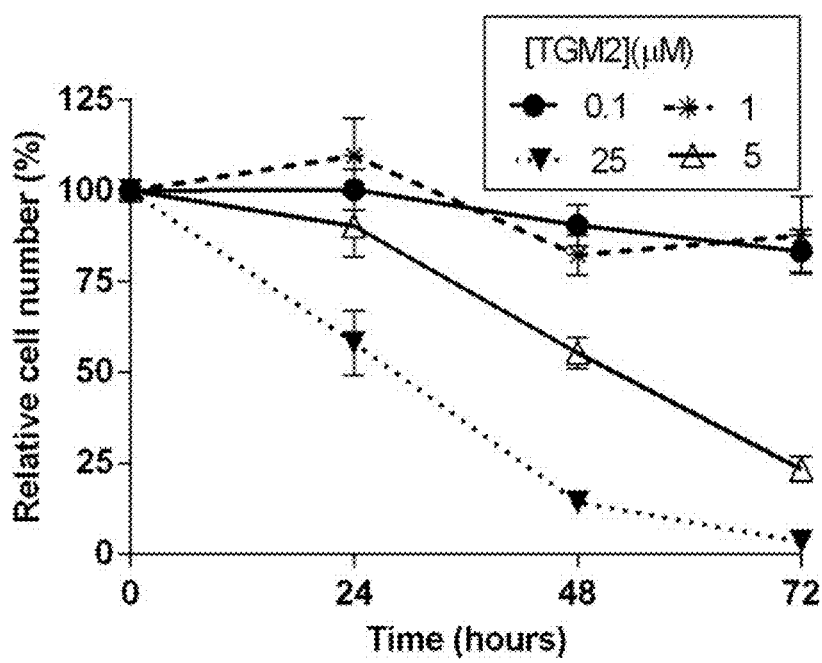
Figure 2:
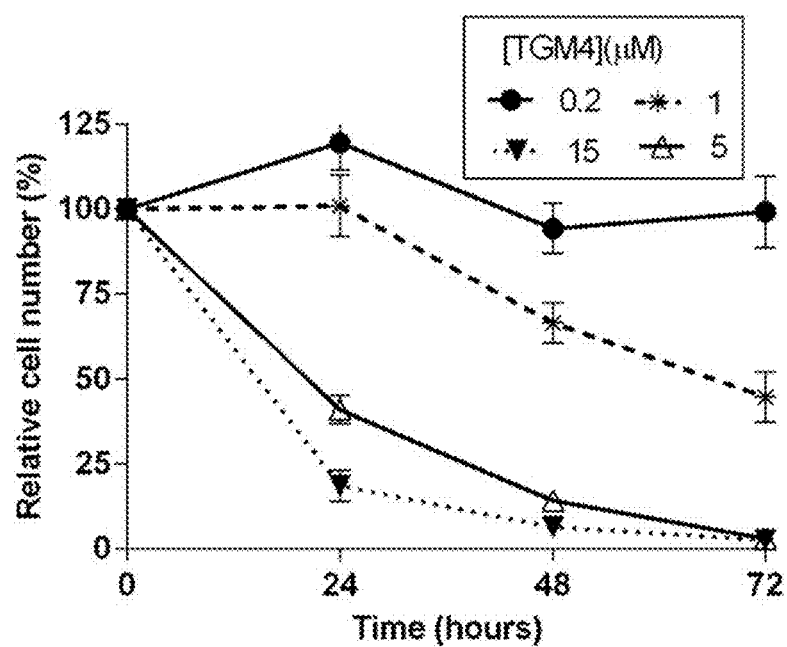
Figure 2:
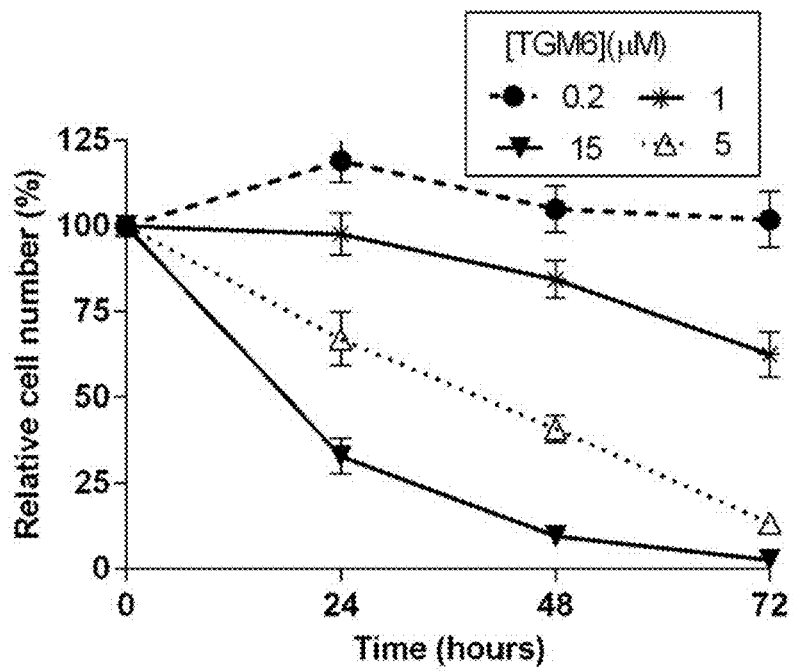

On the one hand, human cells of different types of cancer were used. The cells were incubated at 37° C. and 5% of $CO_2$ in air, in culture medium RPMI1640 or DMEM with bovine foetal serum (10%) and other supplements and in the presence or absence of the triglycerides of the present invention at different concentrations during 72 hours. It was possible to observe that the hydroxy-triglycerides of the invention have a high efficacy against the growth of human tumour cells, but not against the growth of normal non-tumour cells (human fibroblasts, MRC5). In this way, the molecules of the invention presented efficacy to stop the growth of lung cancer, cerebral glioma, neuroblastoma (central nervous system), breast cancer, prostate cancer, pancreatic cancer, leukaemias (lymphomas and myelomas), cervical cancer, cancer of the colon and liver cancer, but they did not present noteworthy activity against non-tumour cells (MRC5) (FIG. 2 and Table 2).

ment of certain types of tumours, but lack a therapeutic effect, once the cancer has developed. In contrast, the hydroxy-triglycerides have a high antitumor efficacy, as demonstrated by these and other results shown further below. Both in the case of the natural triglyceride (triolein) and in the case of the hydroxy-triglycerides no relevant inhibiting effect is observed on the growth of normal non tumour cells (MRC-5 cells). These data justify the absence of toxicity that all these molecules have at therapeutic doses.

B) In Vivo Model

Figure 3:
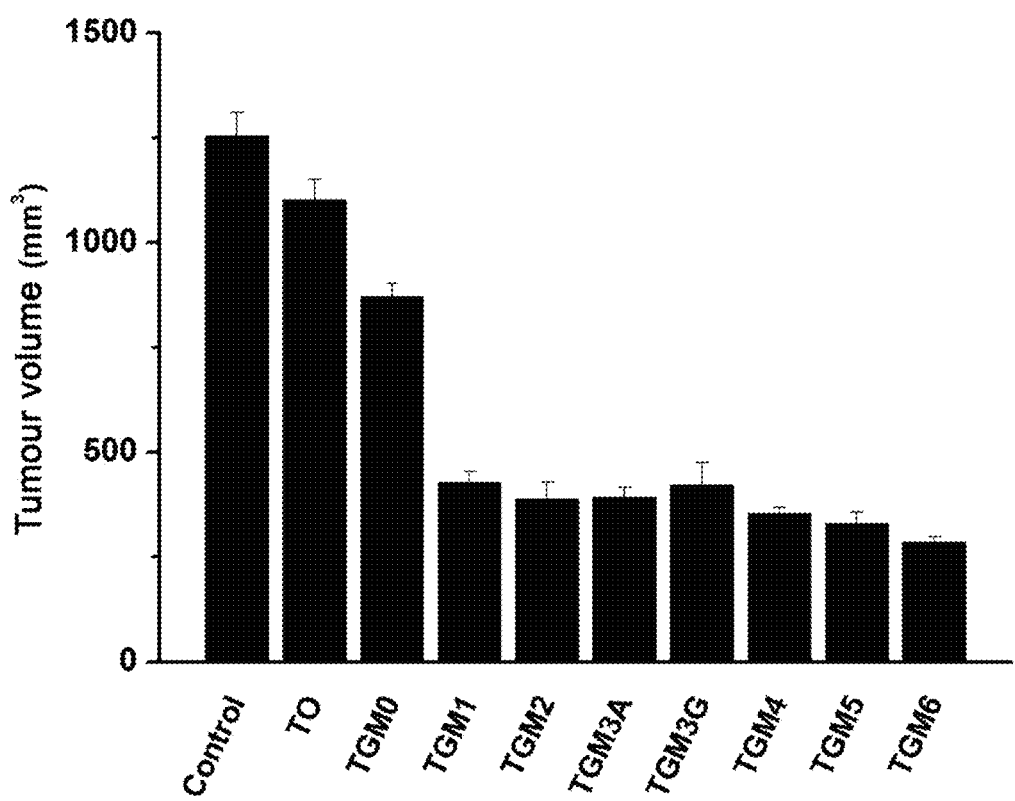
FIG. 3. Antitumor efficacy, measured as final volume of the tumour ($mm^3$), of the hydroxy-triglycerides TGM0, TGM1, TGM2, TGM3A, TGM3G, TGM4, TGM5 and TGM6 of the present invention vs. the natural triglyceride, triolein TO, in an animal model of human lung cancer (A549).

On a separate note, to confirm the antitumor efficacy of the hydroxy-triglycerides in vivo, nude immunosuppressed rats were used {[Crl:Nu(Ico)-Fox1] Nu/Nu} in which human non-microcytic lung cancer cells were implanted by injection ($5 \times 10^6$ cells A549 per animal). The size of the tumours was measured for the first time 10 days after implanting the human tumour cells, once the tumours became visible. As of that moment, the animals were treated with vehicle (water: Control), or with 400 mg/kg (oral, once a day) of triolein (TO) or the different hydroxy-triglycerides indicated above (Table 1) and the volume of the tumours was monitored during 28 days. FIG. 3 shows the final volume of the tumour ($mm^3$) measured with a digital Vernier calliper gauge. The volume of the tumours was calculated using the following equation:

$$v = w^2 \times l / 2$$

TABLE 2

Antitumor effect of the molecules of the hydroxy-triglycerides[a]

|  | Trilolein | TGM0 | TGM1 | TGM2 | TGM3A | TGM3G | TGM4 | TGM5 | TGM6 |
|---|---|---|---|---|---|---|---|---|---|
| A549 (lung) | >500 | 121 | 29 | 2 | 43 | 39 | 0.9 | 4 | 1 |
| NCI1975D (lung) | 466 | 327 | 292 | 54 | 64 | n.d. | 10 | 14 | 21 |
| SF767 (glioma) | >500 | 278 | 282 | 31 | 57 | 46 | 21 | 26 | 41 |
| U87M (glioma) | >500 | 342 | 257 | 56 | 31 | 28 | 17 | 43 | 36 |
| MDA-MB231 (breast) | 381 | 254 | 128 | 57 | 116 | 187 | 36 | 18 | 9 |
| PC3 (prostate) | >500 | 231 | 240 | 42 | 119 | 94 | 18 | 21 | 5 |
| BXPC3 (pancreas) | >500 | 297 | 211 | 31 | 80 | 81 | 72 | 17 | 18 |
| MIA-PaCa-2 (pancreas) | >500 | 283 | 144 | 77 | 142 | 123 | 43 | 23 | 29 |
| Jurkat (lymphoblastic leukaemia) | 492 | 176 | 32 | 67 | 95 | 174 | 151 | 9 | 25 |
| HL-60 (myeloblastic leukaemia) | >500 | n.d. | 243 | 114 | 58 | 42 | 32 | 13 | 6 |
| HeLa (cervix) | >500 | 199 | 184 | 147 | 164 | 75 | 6 | 19 | 12 |
| HT-29 (colon) | >500 | 265 | 93 | 132 | 187 | 59 | 11 | 8 | 34 |
| SH-SY5Y (neuroblastoma) | >500 | 253 | 129 | 74 | 39 | 154 | 27 | 29 | 7 |
| HepG2 (liver carcinoma) | >500 | 326 | 87 | 25 | 42 | 187 | 22 | 52 | 30 |
| MRC5 (non-tumour) | >500 | >500 | >500 | >500 | >500 | >500 | >500 | >500 | >500 |

[a]The growth inhibition corresponds to $IC_{50}$ values (micromolar concentration) which reduces the number of cells to 50% following 72 hours of incubation.
n.d.: not determined.

In particular, FIG. 2 shows the inhibition of growth of human lung cancer cells (A549) produced by molecules (A) TGM1, (B) TGM2, (C) TGM4 and (D) TGM6 depending on concentration and the time of incubation. Similar experiments were made with the rest of TGMs of the invention for different types of tumour cells (see Table 2). Said Table 2 shows the $IC_{50}$ values of each one of the hydroxy-triglycerides versus the cell growth of various types of cancer. The $IC_{50}$ value is the concentration that reduces the number of tumour cells by half. As can be appreciated from the table, the hydroxy-triglycerides (TGM) are capable of inhibiting the growth of tumour cells with high power. In contrast, natural triglycerides, like triolein (main triglyceride of olive oil), has a low or nil power to inhibit the growth of tumour cells.

These results explain the fact that olive oil and other natural oils have a preventative effect against the developwhere v is the volume of the tumour, w is the width and l is the length thereof. The number of animals in all the groups was 8. As can be appreciated from FIG. 3, the tumour growth inhibition produced by the natural triglyceride, triolein, is modest, while the antitumor effect of the hydroxy-triglycerides of the invention is very marked and was significant (P<0.01): in all cases, it was possible to observe that the molecules of the invention reduced the volume of the tumours without killing the animals, which demonstrates that they are effective for the treatment of cancer. In addition to inducing significant reductions in the tumours, these molecules can be administered orally and lack relevant toxicity at therapeutic doses, as they did not produce toxic effects on non-tumour cells or on the test animals. These results set out in FIGS. 2 and 3 and in Table 2 clearly indicate that the hydroxy-triglycerides are effective for the treatment and prevention of different types of cancer through nutraceutical and pharmaceutical approaches.

Example 3. Use of the Hydroxy-Triglycerides of the Invention in the Prevention and/or Treatment of Metabolic and Cardiovascular Pathologies Metabolic and cardiovascular pathologies are closely related. The overfeeding which characterises our society not only gives rise to problems of obesity and excess weight. It is also linked to the appearance of diabetes, dyslipidaemia, hypertension, strokes, arteriosclerosis, ictus, etc. All of these pathologies increase the risk of premature death and can even cause death. In this sense, certain natural oils show a certain efficacy against this type of pathologies, but their power is limited. In contrast, the molecules of the invention have an important effect against the development of this type of pathologies. To be able to study the effects of the compounds of the invention for the prevention and treatment of metabolic and cardiovascular pathologies, hypertensive rats were used (SHR strain, spontaneously hypertensive rats). These rats present obesity, high blood pressure, dyslipidaemia (hypercholesterolemia and hypertriglyceridemia), diabetes, metabolic syndrome and other related health problems.

A) Effect of the Compounds of the Invention on Blood Pressure.

Figure 4:
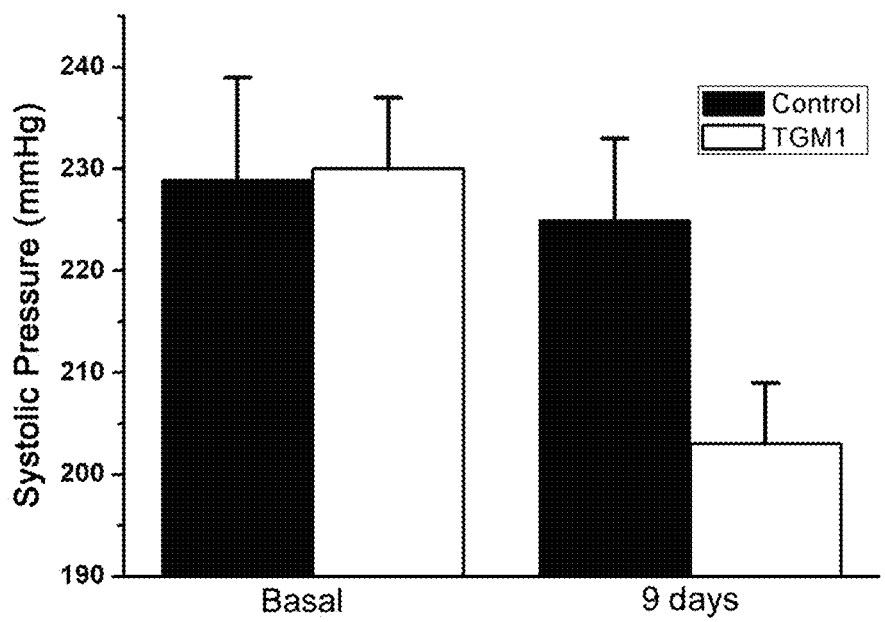
FIG. 4. Effect of TGM1 (400 mg/kg, every 12 h, p.o.) on blood pressure in spontaneously hypertensive rats (of the spontaneously hypertensive rats strain, SHR), measured as the systolic pressure before starting treatment (basal) and 9 days later.

Hypertensive rats of the SHR strain (spontaneously hypertensive rats) with an approximate weight of 300 grams were treated with TGM1 during 9 days (400 mg/kg, every 12 h, p.o.). Systolic pressure was measured before starting the treatment (basal) and 9 days later. In these animals with a metabolic/cardiovascular pathology, this treatment with TGM1 produced drops in blood pressure of approximately 25 mmHg, while the 14-day treatments with 600 mg/kg of TGM1 induced even greater drops in systolic blood pressure of up to 37 mmHg for TGM1 and up to 52 mmHg for TGM6 (FIG. 4 and Table 3). This hypotensive effect clearly indicates that the molecules of this invention have a high potential for the prevention and treatment of cardiovascular pathologies, and that the TGMs of the present invention can be used for the prevention and treatment of hypertension at nutraceutical and pharmaceutical level.

B) Effect of the Compounds of the Invention on Glucose Levels.

Figure 5:
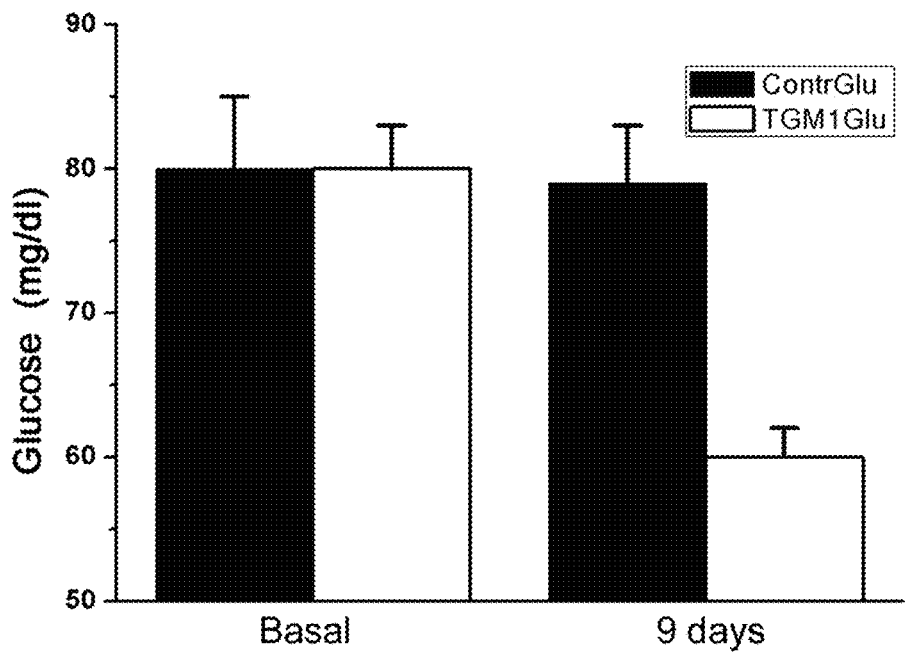
FIG. 5. Effect of TGM1 (400 mg/kg, every 12 h, p.o.) on the glucose levels in spontaneously hypertensive rats (of the spontaneously hypertensive rats strain, SHR), measured as plasma glucose before starting treatment (basal) and 9 days later.

At the same time, research was conducted into the efficacy of the hydroxy-triglycerides for controlling the high levels of glycaemia in SHR rats, and therefore, preventing or curing diabetes. Hypertensive rats (SHR) with an approximate weight of 300 grams were treated with TGM1 during 9 days (400 mg/kg, every 12 h, p.o.). Plasma glucose was measured before starting the treatment (basal) and 9 days later. In all cases, the plasma measurements were conducted in rats kept fasting during 12 hours. In this way, after 9 days of treatment, the levels of glucose in blood were reduced by up to more than 25% for the molecules of the invention (FIG. 5 and Table 4).

TABLE 4

Effect of the hydroxy-triglycerides on the levels of glucose in plasma

|                  | Control | TGM0 | TGM1 | TGM2 | TGM3A | TGM3G | TGM4 | TGM5 | TGM6 |
| ---------------- | ------- | ---- | ---- | ---- | ----- | ----- | ---- | ---- | ---- |
| Δ G (mg/dl)[a]   | −1      | −4   | −20  | −7   | −14   | −9    | −5   | −13  | −16  |

[a]Change in glucose levels from the start of treatment (basal value) and after 9 days of treatment with 400 mg/kg (every 12 hours, p.o.).

Thus, SHR rats have blood glucose levels higher than those presented by normal rats and this diabetic condition can be regulated by the TGMs described in the present invention. These results clearly demonstrate that the TGMs of the present invention are capable of regulating the glycaemic index, normalising high values of glucose in blood. Through this, these results demonstrate that hydroxy-triglycerides are effective for the prevention and treatment of diabetes, through nutraceutical and pharmaceutical approaches.

C) Effect of the Compounds of the Invention on Cholesterol and Lipid Levels.

Also, SHR rats were used to research the efficacy of the hydroxy-triglycerides for the prevention and treatment of dyslipidaemias. On the one hand, treatments with different oral doses and durations gave rise to reductions in the plasma levels of total cholesterol and its fractions in test animals (Tables 5 and 6). These reductions were marked and significant, returning the cholesterol in plasma values to those found in animals without metabolic/cardiovascular disorders. These results indicate that the molecules of the present invention are useful for the prevention and the treatment of hypercholesterolemia.

TABLE 3

Effect of the hydroxy-triglycerides on systolic blood pressure

|                   | Control | TGM0 | TGM1 | TGM2 | TGM3A | TGM3G | TGM4 | TGM5 | TGM6 |
| ----------------- | ------- | ---- | ---- | ---- | ----- | ----- | ---- | ---- | ---- |
| Δ SP (mmHg)[a]    | −4      | −8   | −37  | −41  | −28   | −21   | −43  | −40  | −52  |

[a]Change in systolic blood pressure in hypertensive rats (SHR) at the start of the treatment (basal value) and after 14 days of treatment with 600 mg/kg (every 12 hours, p.o.). The average basal value for systolic pressure in these animals was 216 mmHg.

TABLE 5

Effect of TGM1 on levels of cholesterol in plasma

|  | Control | TGM1 |
|---|---|---|
| Total cholesterol (mmHgmg/dl)[a] | 72.77 ± 4.908 | 49.11 ± 3.084 |
| HDL (mmHgmg/dl) | 44.81 ± 1.522 | 33.44 ± 2.251 |
| LDL (mmHgmg/dl) | 3.788 ± 0.3189 | 3.644 ± 0.3244 |

[a]Plasma values of total cholesterol and of the high-density lipoprotein (HDL) and low-density lipoprotein (LDL) forms in plasma of SHR control rats and treated with TGMs during 14 days (600 mg/kg, 12 h, p.o.).

TABLE 6

Effect of the hydroxy-triglycerides on the levels of total Cholesterol in plasma

|  | Control | TGM0 | TGM1 | TGM2 | TGM3A | TGM3G | TGM4 | TGM5 | TGM6 |
|---|---|---|---|---|---|---|---|---|---|
| Chol (mg/dl)[a] | 79.3 ± 3 | 62.2 ± 3 | 55.5 ± 2 | 51.7 ± 2 | 49.8 ± 2 | 65.1 ± 4 | 72.7 ± 2 | 58.4 ± 3 | 48.9 ± 3 |

[a]Levels of cholesterol in plasma in SHR control rats and treated with TGMs during 6 days (400 mg/kg, p.o.).

Similarly, oral treatments with the hydroxy-triglycerides of the present invention reduced the levels of triglycerides in the plasma of SHR rats (Table 7). These results demonstrate that the molecules of the present invention are useful for the prevention and treatment of hypertriglyceridemia. Also, along with the effects of the hydroxy-triglycerides on cholesterol levels shown above, these results show that the molecules of the present invention can be useful for the prevention and treatment of dyslipidaemias in general.

TABLE 7

Effect of the hydroxy-triglycerides levels of Triglycerides in plasma

|  | Control | TGM0 | TGM1 | TGM2 | TGM3A | TGM3G | TGM4 | TGM5 | TGM6 |
|---|---|---|---|---|---|---|---|---|---|
| TG (mg/dl)[a] | 84.2 ± 6 | 69.7 ± 7 | 51.6 ± 4 | 61.7 ± 3 | 54.8 ± 4 | 64.1 ± 5 | 69.3 ± 3 | 56.2 ± 3 | 49.4 ± 4 |

[a]Change in the levels of triglycerides in plasma of SHR control rats and treated with TGMs during 6 days (400 mg/kg, p.o.).

D) Effect of the Compounds of the Invention on Body Weight.

Finally, the hydroxy-triglycerides of the present invention induced reductions in the body weight of SHR rats following two weeks of oral treatment (Table 8). These results demonstrate that the molecules of the present invention are useful for the prevention and treatment of obesity and excess weight.

TABLE 8

Effect of the hydroxy-triglycerides on body weight

|  | Control | TGM0 | TGM1 | TGM2 | TGM3A | TGM3G | TGM4 | TGM5 | TGM6 |
|---|---|---|---|---|---|---|---|---|---|
| ΔWeight (g)[a] | +3.7 ± 2 | −4 ± 2 | −22 ± 5 | −32 ± 6 | −14 ± 4 | −12 ± 3 | −25 ± 5 | −9 ± 3 | −19 ± 4 |

[a]Change in weight (grams) of SHR control rats and treated with TGMs during 14 days after administering vehicle (Control) or the hydroxy-triglycerides (600 mg/kg, 12 h, p.o.). The average basal weight of the animals was 342 grams.

Metabolic syndrome is a disease characterised by the concurrence of various metabolic and cardiovascular pathological conditions, which include obesity, hypertension, hypercholesterolemia, hypertriglyceridemia, diabetes, etc. (Kaur, 2014). Currently, the possibilities for treatment of metabolic syndrome are limited, as medicine is usually applied for each one of the symptoms that the patient presents. The efficacy shown by the hydroxy-triglycerides of the present invention to reduce body weight, high blood pressure, glucose levels, cholesterol and triglycerides demonstrate that the molecules of the present invention can be tools of great value for the prevention and treatment of metabolic syndrome.

The set of health problems that appear in SHR rats and other strains of rats demonstrate that metabolic and cardiovascular pathologies are related. As currently each symptom is treated separately, patients who have metabolic and cardiovascular pathologies receive a high number of medicines which can endanger the health of their liver. The hydroxy-triglycerides have shown efficacy against all the cardiovascular metabolic disorders studied. For this reason, it is possible to conclude that the molecules of the present invention are effective to prevent and treat diseases of a metabolic and cardiovascular nature, such as for example hypertension, atherosclerosis, arteriosclerosis, strokes, ictus, arrhythmia, hypertriglyceridemia, hypercholesterolemia and other dyslipidaemias, obesity, diabetes, metabolic syndrome, etc., through pharmaceutical and nutraceutical approaches.

Example 4. Use of the Hydroxy-Triglycerides of the Invention in the Prevention and/or Treatment of Neurodegenerative Pathologies Neurodegenerative pathologies include various types of disorders, such as Alzheimer's disease, Parkinson's disease, Huntington's disease, different types of dementia, different types of sclerosis, adult polyglucosan body disease (APBD), neuropathic pain, spinal injury, aging, etc. Numerous neurological diseases tend to produce inflammation and, in the opposite direction, inflammation produces neurological problems of various types, mainly pain. The fact that certain neurodegenerative diseases, such as Alzheimer's disease, give rise to inflammatory processes is notorious and it has even been demonstrated that this disease would be in part produced by inflammatory processes (Krstic and Knuesel, 2013; Liu and Chan, 2014). In most cases of neurodegenerative processes, alterations have been found in the levels of membrane lipids (Mielke and Lyketsos, 2010). The hydroxy-triglycerides of the present invention have the capacity to restore the lipid balance in the membranes of the neurons and, through this, to contribute to the prevention and treatment of these pathologies.

A) Effect of the Compounds of the Invention on the Activity of Glycogen Branching Enzyme 1 (GBE1).

It has been possible to observe that the molecules of the present invention are capable of regulating the activity of the Glycogen Branching Enzyme 1 (GBE1) and its joining to membranes (Table 9). Alterations in this enzyme give rise to a neurodegenerative process known as APBD (Kakhlon et al., 2013). It has been described that a modification of tyrosine in position 329 of this enzyme (Y329S) causes a reduction in the activity of GBE1. This gives rise to a lower branching of glycogen, which precipitates forming glucose bodies which interfere with cell activity (Kakhlon et al., 2013). This gives rise to problems in the function of certain organs, to motor problems and, in some cases, to cognitive decline. We have been able to verify that the hydroxy-triglycerides of the present invention are capable of regulating the joining of native GBE1 (wild type, wt) and with the variant Y329S to membranes and to increase the activity of the form Y329S, which is very low in normal conditions (Table 9). For this reason, the molecules of the present invention are effective for the prevention and treatment of the polyglucosan bodies disease, APBD.

of age, affecting approximately one third of people over the age of 80. It has been observed that in the brains of patients with Alzheimer's disease there are lipid alterations which would affect the levels of phosphatidylethanolamine and of the unsaturated fatty acids (Guan et al., 1999). Also, the neurodegenerative process is associated to an inflammatory process in the brain, which would accelerate the death of neurons (Hoozemans et al., 2011).

In order to study Alzheimer's disease a transgenic rat model was used with 5 mutations which appear in human familiar Alzheimer's (symbolised as Tag, and abbreviated Tg). This model of Alzheimer's is very severe, and the animals already show a cognitive deficit at 2 months of age. To carry out this experiment, both young rats (of 3 months of age) and aged rats (of 10 months of age) were used and treated for 3 months with the hydroxy-triglycerides of the present invention (50 mg/kg day, p.o.). The rats were subjected to a low-calorie diet so that they would be hungry and carry out a test in a radial maze, in which food was placed in 4 of the device's 8 arms (asymmetrically), quantifying the number of errors committed until the exercise was completed. The number of errors committed by the rats during the first week of the tests was considered to be 100%.

Figure 7:
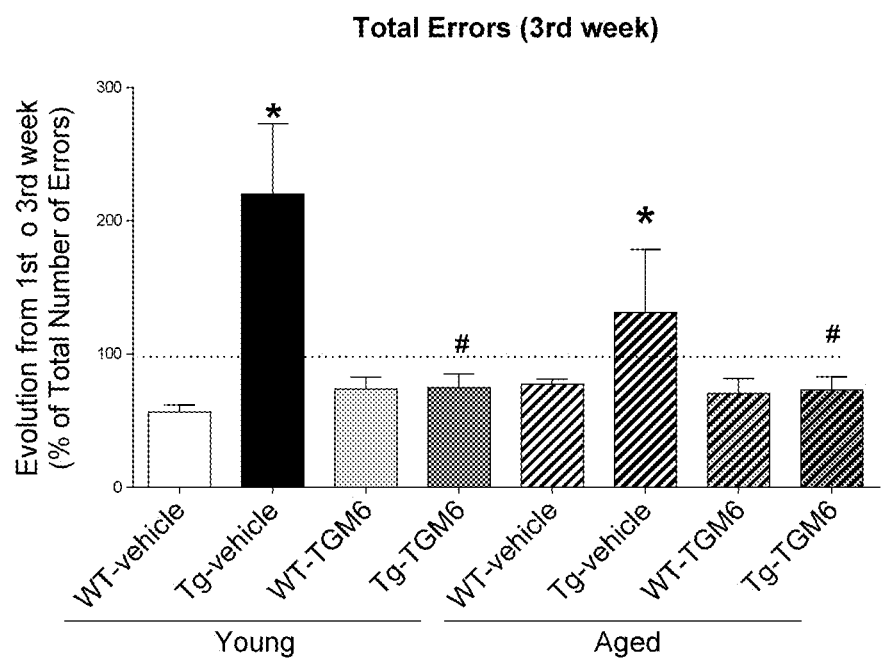
FIG. 7. Effect of TGM6 against Alzheimer's disease. A. Percentage of errors committed on completing a test in a radial maze (in which food was placed in 4 of the 8 arms of the device) by healthy rats (WT, wild type) and rats with Alzheimer's [Tg, transgenic rat with 5 mutations which appear in human familial Alzheimer's (tag)] treated with vehicle (vehicle=water) or the hydroxy-triglyceride TGM6 (for 3 months with 50 mg/kg day, p.o.), both in young rats (Young, of 3 months of age) and aged (Aged, of 10 months of age), during the third week of tests; B. Effect of TGM6 on the cognitive parameters and aging in *Drosophila melanogaster* with human Alzheimer's genes measured in a geotaxis test, as the percentage of animals that climbed inside a glass pipe to above a mark situated about 15 cm from the base in a period of 20 seconds and as a function of age (days).
Figure 7:
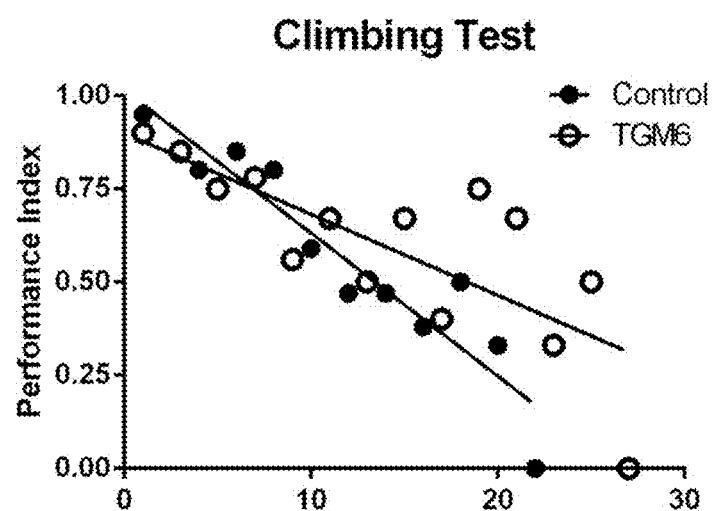

In this sense, treatments with hydroxy-triglycerides allow for normalisation of the lipids of the neuronal membranes and reduce the neuro-inflammation (related to the appearance of senile plaques), which gives rise to the recovery of the cognitive parameters of the transgenic rats with human Alzheimer's originated by the presence of 5 characteristic mutations of human familiar Alzheimer's. In these animals, the hydroxy-triglycerides of the present invention produced improvements in the cognitive parameters of both young animals with incipient Alzheimer's and in aged rates with an advanced pathological condition (FIG. 7 and Table 10). For example, in young and aged rats it is possible to appreciate from FIG. 7A how TGM6 not only improved significantly the cognitive results of the exercise, but also even produced

TABLE 9

Effect of the hydroxy-triglycerides on the enzyme GBE1

| | Control | TGM0 | TGM1 | TGM2 | TGM3A | TGM3G | TGM4 | TGM5 | TGM6 |
|---|---|---|---|---|---|---|---|---|---|
| Activity GBE1wt[a] | 100 ± 3 | 95 ± 12 | 89 ± 10 | 72 ± 5 | 88 ± 2 | 69 ± 7 | 31 ± 4 | 24 ± 2 | 33 ± 3 |
| Activity Y329S[a] | 13 ± 2 | 20 ± 2 | 7 ± 1 | 11 ± 2 | 10 ± 2 | 9 ± 4 | 4 ± 1 | 16 ± 3 | 5 ± 1 |

[a]Activity of the purified enzyme (nmol/min · ng pure protein) in the presence of PC membranes with the TGMs of the invention (20 mol %). The activity of the non-mutated enzyme (GBE1) is considered to be 100% (0.76 nmol/min · ng protein).

B) Effect of the Compounds of the Invention on Alzheimer's Disease in Rats.

Alzheimer's disease is a neurodegenerative pathology which gives rise to a cognitive decline of its patients and a gradual loss in their quality of life. This disease has a high social and clinical cost, also indirectly affecting the relatives of the ill. Its incidence doubles every 4-5 years as of 60 years improvements in the execution thereof over time (reduction in the number of errors below 100%. Similarly, the rest of TGMs also produced significant improvements in the execution of the cognitive test (Table 11) meaning that the cognitive recovery with some of these molecules was total, noting cognitive values similar to those of healthy animals (100%).

TABLE 10

Effect of the hydroxy-triglycerides on the cognitive parameters of rats with Alzheimer's

| | Control | TGM0 | TGM1 | TGM2 | TGM3A | TGM3G | TGM4 | TGM5 | TGM6 |
|---|---|---|---|---|---|---|---|---|---|
| Errors (%)[a] | 207.6 | 153.1 | 128.9 | 143.2 | 134.5 | 156.8 | 101.0 | 121.3 | 84.7 |

[a]Errors made in the radial maze by Tag rats (with Alzheimer's) before completing the exercise. Each test group had 8 animals and the percentage is indicated. The value of 100% corresponds to healthy animals without Alzheimer's.

The control animals were treated with vehicle (saline) and the rest with 50 mg/kg (p.o.) daily of the indicated compound.

C) Effect of the Compounds of the Invention on Cognitive Parameters and Survival in *Drosophila melanogaster* Flies Having Alzheimer's Disease Genes.

To investigate the effect of TGMs on the cognitive parameters and aging, another model of Alzheimer's disease in *Drosophila melanogaster* flies with genetic alterations corresponding to human Alzheimer's was used. The flies used were the first generation (F1) from the crossing of UAS-Aβ human-Tau 2N4R (stock 33771) flies with elav-GAL4$^{c155}$ (stock 8760) flies. This model which over-expresses the two proteins typical of Alzheimer's disease is complementary to the model described above and very convenient, as these animals have a life of approximately 1 month and it is possible to add the compounds to the food of the larvae to see the preventative effect thereof throughout their entire life. Also, it allows the effect on aging to be seen and on the life expectancy of these animals (survival over time).

In this sense, the flies with human Alzheimer's (F1) present a greater cognitive decline in comparison to the "Oregon" fly strain, which are the healthy controls. To evaluate the effect of the hydroxy-triglycerides of the invention, each one of the TGMs (100 μM) was added to the food consumed by these animals. It was possible to observe a positive effect of same in the geotaxis test of climbing (FIG. 7B and Table 11). In this test, the behavioural motor activity was investigated in 25 flies treated with vehicle or one of the TGMs. In this study, the flies were introduced in a glass cylinder with an opening closed with a sponge so air could enter. The flies were taken to the ground (bottom) of the pipe by giving it a sharp blow on a table and their behaviour was timed during 20 seconds. Once this time was over, the number of flies which had passed (crossed) a mark at 15 cm from the bottom was counted (geotaxis test). Usually, more than 90% of healthy young flies passed the line within 20 seconds. However, with aging or with Alzheimer's disease, the behavioural motor activity (percentage of flies which crossed the line) declined, compared to normal flies. In this context, the treatments with the hydroxy-triglycerides of the present invention avoided this cognitive decline associated to Alzheimer's, making the cognitive capacity of the diseased flies similar to that of the healthy flies. In particular, the treatment with TGM6 induced a recovery in cognitive parameters, making the climbing test practically indistinguishable from that observed in normal flies (FIG. 7B). This positive effect on the cognitive parameters in flies was also shown by other TGMs (Table 11). In fact, in the control group with Alzheimer, no fly crossed the line as of 23 days of age. In this sense, the different hydroxy-triglycerides induced marked increases in the geotaxis test values, with increases in the cognitive values which reached up to 36 days, 50% more in the life of the flies with Alzheimer's (Table 11).

These results demonstrate that the compounds of the present invention are effective for the prevention and treatment of the negative effects of aging, in general, and of Alzheimer's disease, in particular. On a separate note, the survival of *D. melanogaster* flies with Alzheimer's disease was 28 days, on average. The treatment with the hydroxy-triglycerides of the present invention produced increases in the life expectancy of up to 45 days, in other words, of more than 50% in reference to the control animals. These results demonstrate that the reduction in the neurodegenerative processes give rise to a marked increase in the life expectancy of the animals, from which it can be considered that the molecules of the present invention are effective for the treatment of physiological and pathological aging. Thus, these results demonstrate that the compounds of the present invention are effective for the prevention and treatment of neurological problems in general and Alzheimer's disease, in particular.

Figure 6:
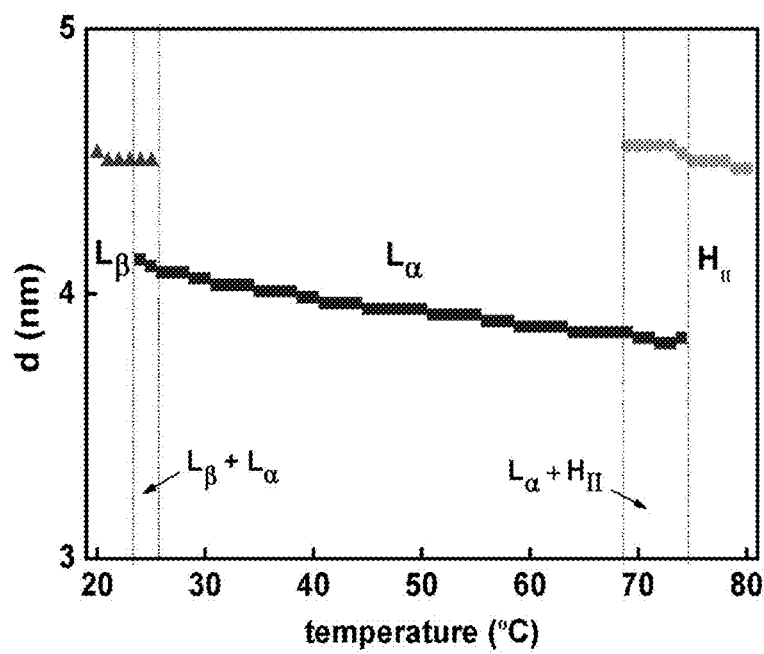
FIG. 6. Effect of the hydroxy-triglycerides on the membrane structure determined by X-ray diffraction (small angle, SAXS) studies of palmitoyl-oleoyl phosphatidylethanolamine in A. absence; or presence of 5 mol % of B. TGM1; C. TGM2; D. TGM4; or E. TGM6, wherein the separation [d, (nm)] of the lipid layers is measured as a function of temperature (° C.): $L_\alpha$=liquid lamellar phase; $L_\beta$=solid lamellar phase; $L_\beta+L_\alpha$=solid lamellar to liquid lamellar transition; $L_\alpha+H_{II}$=lamellar-to-hexagonal transition; $H_{II}$=hexagonal inverse phase.
Figure 6:
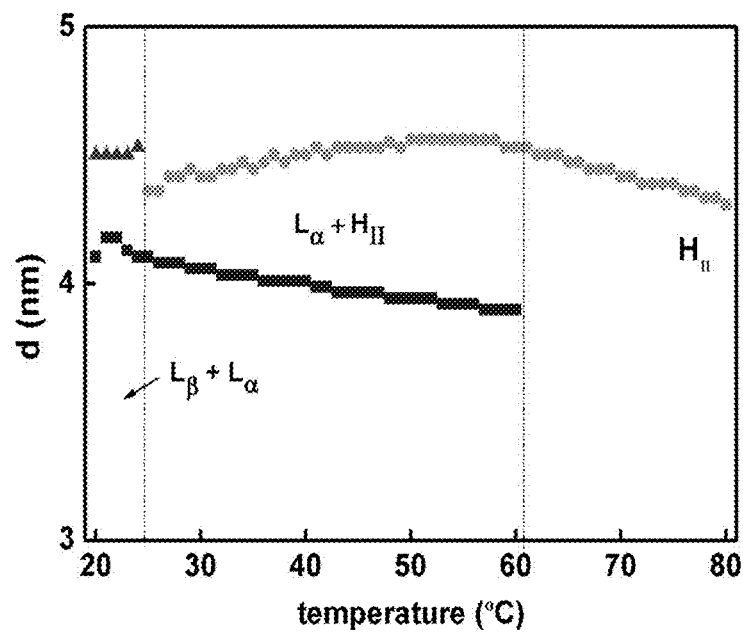
Figure 6:
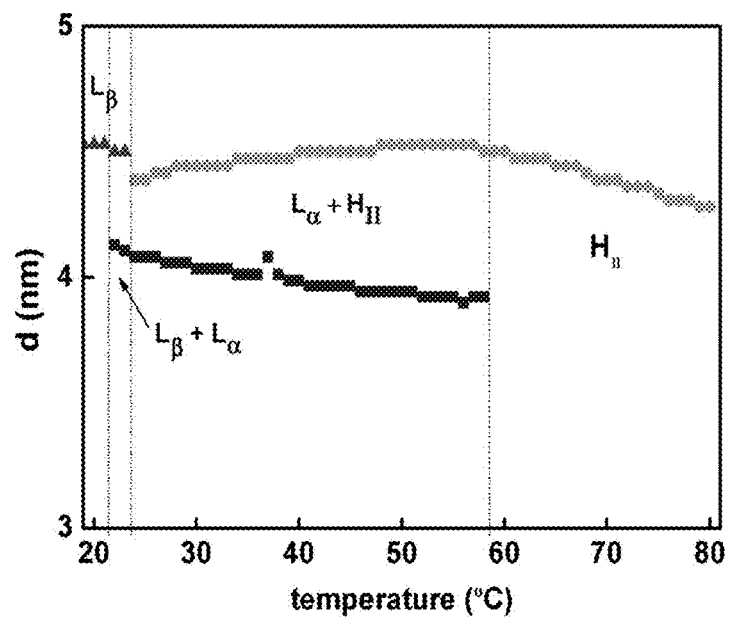
Figure 6:
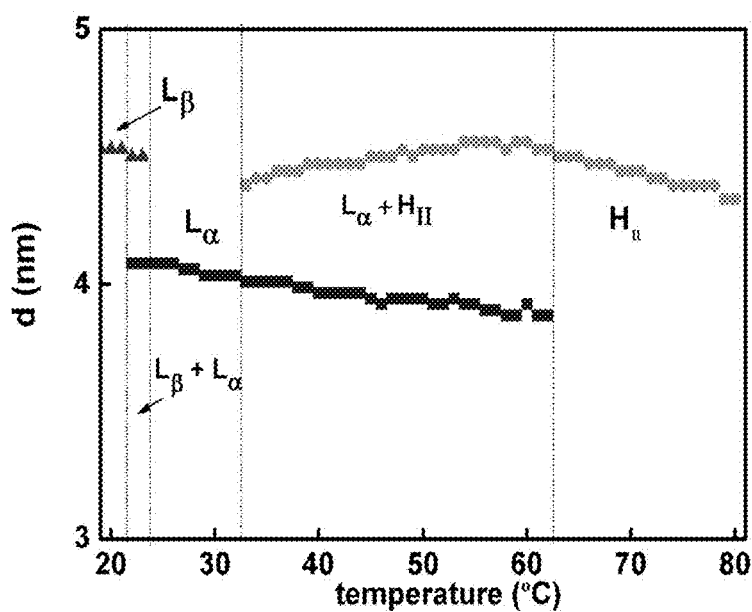
Figure 6:
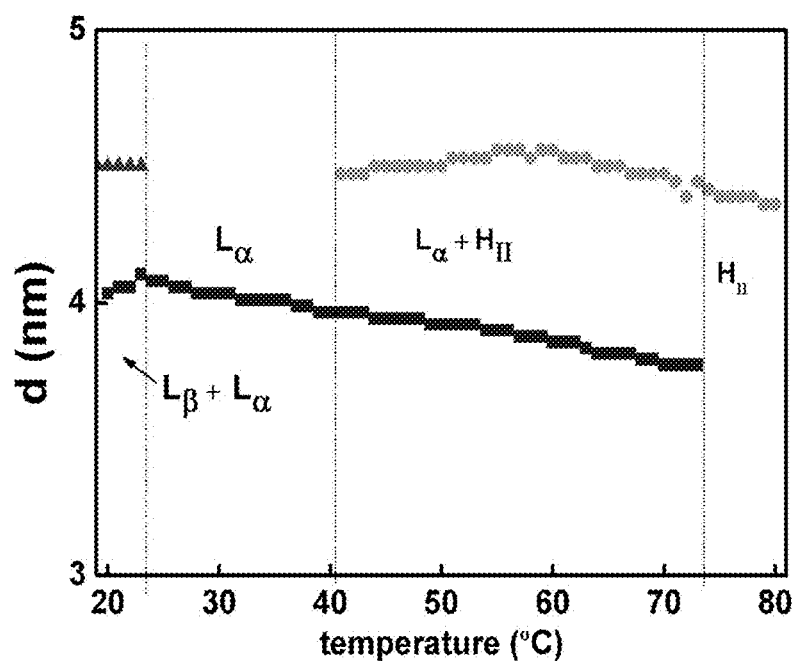

Example 5. Effect of the Hydroxy-Triglycerides of the Invention on the Membrane Structure This experiment shows the biophysical properties of the membrane without TGM or with TGMs with X-ray diffraction studies (small angle, SAXS) of palmitoyl-oleoyl phosphatidylethanolamine in the absence or presence of 5 mol % of TGM1, TGM2, TGM4 or TGM6 (FIG. 6). As can be appreciated, the presence of TGM induce a very important reduction in the lateral surface tension which is evident from the reduction in the value of the lamellar-to-hexagonal (L-a-H$_{II}$) transition temperature, which in turn indicates an increase in non-lamellar propensity: Table 12). This effect has an important repercussion on the functionality of the membrane, as this structure allows for the anchoring of certain membrane proteins necessary for cell signalling. For this reason, it can be said that the TGMs have a positive effect on cell signalling because they allow the propagation of cell signals which are lost in association with a wide variety of diseases. This effect shown on the structure of the membrane explains in part why certain oils, such as olive oil or fish oil, have important beneficial properties for the prevention of various diseases, such as cancer, cardiovascular/metabolic diseases and neurological/neurodegenerative diseases. FIG. 6 and Table 12 show clearly how all the TGMs have a similar effect, although with minor nuances in each case. The effect on the solid-liquid transition (Tm) and the lamellar to hexagonal transition (T$_H$) was measured in membranes of palmitoyl-oleoyl phosphatidylethanolamine (POPE) by means of X-ray diffraction in the absence of (POPE Control) or presence of 1 mol % of each one of the indicated TGMs.

TABLE 11

Effect of the hydroxy-triglycerides on the cognitive parameters of *D. melanogaster* with Alzheimer's disease

| | Control | TGM0 | TGM1 | TGM2 | TGM3A | TGM3G | TGM4 | TGM5 | TGM6 |
|---|---|---|---|---|---|---|---|---|---|
| Geotaxis (%)$^a$ | 23 | 25 | 32 | 29 | 36 | 29 | 35 | 26 | 28 |
| Survival (d)$^b$ | 28 | 30 | 45 | 33 | 40 | 31 | 44 | 31 | 39 |

$^a$Age (days) at which the animals showed a geotaxis of nil (no fly passes the line marked on the tube).
$^b$Age (days) at which all the animals in the group died.

TABLE 12

| Transition temperatures of POPE with 1 mol % of TGM | | | |
|---|---|---|---|
| | $T_m$ (° C.) | $T_H$ (° C.) | Effect on $T_H$ |
| POPE Control | 23.6 ± 0.2 | 69.1 ± 0.5 | — |
| +1 mol % TGM0 | 22.7 ± 0.2 | 68.3 ± 0.6 | ↓1° C. |
| +1 mol % TGM1 | 23.8 ± 0.3 | 66.0 ± 0.9 | ↓3° C. |
| +1 mol % TGM2 | 23.6 ± 0.3 | 62.0 ± 1.1 | ↓7° C. |
| +1 mol % TGM3A | 23.4 ± 0.2 | 63.0 ± 1.1 | ↓6° C. |
| +1 mol % TGM3G | 23.3 ± 0.3 | 63.6 ± 1.1 | ↓5° C. |
| +1 mol % TGM4 | 23.2 ± 0.2 | 64.6 ± 0.8 | ↓5° C. |
| +1 mol % TGM6 | 23.3 ± 0.2 | 64.9 ± 0.9 | ↓4° C. |

Hence, in the present invention, the efficacy of the hydroxy-triglycerides has been demonstrated, which were used successfully in the prevention and/or treatment of diseases whose common aetiology is based on alterations of the plasma lipid profile, as well as on the structure and/or function of the lipids located in the cell membrane. Consequently, interventions on the structure and function of the biological membranes, through the molecules encompassed in the present invention, can modify effectively certain cell functions with the net result of preventing and/or reversing a determined pathological process.

REFERENCES

1. Barone, M., Notarnicola, M., Caruso, M. G., Scavo, M. P., Viggiani, M. T., Tutino, V., Polimeno, L., Pesetti, B., Di Leo, A., Francavilla, A. (2014) Carcinogenesis, in press.
2. Berge, K., Musa-Veloso, K., Harwood, M., Hoem, N., Burri, L. (2014) Nutr. Res. 34, 126-133.
3. Buda, C., Dey, I., Balogh, N., Norvath, L. I., Maderspach, K., Juhasz, M., Leo, Y. K., Farkas, T. (1994) Proc. Natl. Acad. Sci. USA 91, 8234-8238.
4. Escribá, P. V., Sastre, M., García-Sevilla, J. A. (1995) Proc. Natl. Acad. Sci. USA 92, 7595-7599.
5. Escribá, P. V., Sánchez-Domínguez, J. M., Alemany, R., Perona, J. S., Ruiz-Gutierrez, V. (2003) Hypertension 41, 176-182.
6. Escribá, P. V., González-Ros, J. M., Goñi, F. M., Kinnunen, P. K. J., Vigh, L., Sánchez-Magraner, Fernández, A. M., Busquets, X., Horváth, I, Barceló-Coblijn, G. (2008) J. Cell. Mol. Med. 12, 829-875.
7. Féart, C., Samieri, C., Allès, B., Barberger-Gateau, P. (2013) Proc. Nutr. Soc. 72, 140-152.
8. Foulon, V., Sniekers, M., Huysmans, E., Asselberghs, S., Mahieu, V., Mannaerts, G. P., et al. (2005) J. Biol. Chem. 280, 9802-9812
9. Grosso, G., Buscemi, S., Galvano, F., Mistretta, A., Marventano, S., La Vela, V., Drago, F., Gangi, S., Basile, F., Biondi, A. (2013) BMC Surg. 13 Suppl 2, S14.
10. Guan, Z., Wang, Y., Cairns, N. J., Lantos, P. L., Daliner, G., Sindelar, P. J. (1999) J. Neuropathol. Exp. Neurol. 58, 740-747.
11. Gultekin, G., Sahin, H., Inanc, N., Uyanik, F., Ok, E. (2014) Pak. J. Med. Sci. 30, 299-304.
12. Hoozemans, J. J. M., Veerhuis, R., Rozemuller, J. M., Eikelenboom P. (2011) CNS Neurol. Disord. Drug Targets 10, 364-373.
13. Hunter, J. E., Shang, J., Kris-Etherton, P. M. (2010) Am. J. Clin. Nutr. 91, 46-63.
14. Kakhlon, O., Glickstein, H., Feinstein, N., Liu, Y., Baba, O., Terashima, T., Akman, H. O., Dimauro, S., Lossos, A. (2013) J. Neurochem. 127, 101-113.
15. Kaur, J. (2014) Cardiol. Res. Pract. 2014, 943162.
16. Kimura, R., Takahashi, N., Lin, S., Goto, T., Murota, K., Nakata, R., mInoue, H., Kawada, T. (2013) J. Lipid Res. 54, 3258-3268.
17. Kovisto, H. et al. (2014) J. Nutr. Biochem. 25, 157-169.
18. Krstic, D., Knuesel, I. (2013) Nat. Rev. Neurol. 9, 25-34.
19. Lawrence, G. D. (2013) Adv. Nutr. 4, 294-302.
20. Liu, L., Chan, C. (2014) Ageing Res. Rev. 15C, 6-15.
21. Martinez, J., Vögler, O., Casas, J., Barceló, F., Alemany, R., Prades, J., Nagy, T., Baamonde, C., Kasprzyk, P. G., Terés, S., Saus, C. Escribá, P. V. (2005) Mol. Pharmacol. 67, 531-541.
22. Mayneris-Perxachs J., et al. (2014) PLoS One 9, e85202.
23. McDonald, C., Bauer, J., Capra, S., Coll, J. (2014) BMC Cancer 14, 264.
24. Michas, G., Micha, R., Zampelas, A. (2014) Atherosclerosis 234, 320-328.
25. Mielke, M. M., Lyketsos, C. G. (2010) Neuromolecular Med 12, 331-340.
26. Peñalvo, J. L., Moreno-Franco, B., Ribas-Barba, L., Serra-Majem, L. (2012) Eur. J. Clin. Nutr. 66, 795-798.
27. Perona, J. S., Vögler, O., Sánchez-Domínguez, J. M., Montero, E., Escribá, P. V., Ruiz-Gutierrez, V. (2007) J. Gerontol. Biol. Sci. 62a, 256-263.
28. Prentice, A. M. (1998) Am. J. Clin. Nutr. 67 (suppl), 535S-541S.
29. Shah, R. (2013) J. Am. Med. Dir. Assoc. 14, 398-402.
30. Singhal, A., Lanigan, J., Storry, C., Low, S., Birbara, T., Lucas, A., Deanfield, J. (2013) J. Am. Heart Assoc. 2, e000283.
31. West, S. G., Hecker, K. D., Mustad, V. A., Nicholson, S., Schoemer, S. L., Wagner, P., Hinderliter, A L., Ulbrecht, J., Ruey, P., Kris-Etherton, P. M. (2005) Diabetologia 48, 113-122.
32. Whayne, T. F. Jr. (2014) Curr. Cardiol. Rep. 16, 491.
33. Yang, Q., Alemany, R., Casas, J., Kitajka, K., Lanier, S. M., Escribá, P. V. (2005) Mol. Pharmacol. 68, 210-217.
34. Zevenbergen, H., de Bree, A., Zeelenberg, M., Laitinen, K., van Dujin, G., Floter, E. (2009) Ann. Nutr. Metab. 54 Suppl, 15-24.

The invention claimed is:

1. A compound of Formula I, its enantiomers, diastereoisomers, mesomeric compounds, and E/Z isomers thereof:

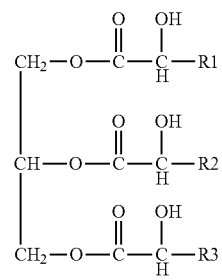

wherein R1, R2 and R3 each and independently, are an aliphatic chain of between 5 and 22 carbon atoms of Formula II:

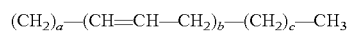

wherein
a is a whole number between 1 and 6;
b is a whole number between 1 and 6; and
c is a whole number chosen from 0, 3 and 6.

2. The compound of Formula I, according to claim 1, wherein said hydrocarbon moieties R1, R2 and R3 each and independently, are an aliphatic chain comprising between 5 and 20 carbon atoms.

3. The compound of Formula I, according to claim 1, wherein said hydrocarbon moieties R1, R2 and R3 each and independently, are an aliphatic chain comprising between 16 and 20 carbon atoms.

4. The compound of Formula I, according to claim 1, wherein
a is a whole number between 1 and 6;
b is a whole number between 2 and 6; and
c is a whole number chosen from 0 and 3.

5. The compound of Formula I, according to claim 1, wherein R1, R2 and R3 each and independently, are selected from a group consisting of $(CH_2)_6—(CH=CH—CH_2)_1—(CH_2)_6—CH_3$, $(CH_2)_6—(CH=CH—CH_2)_2—(CH_2)_3—CH_3$, $(CH_2)_6—(CH=CH—CH_2)_3—CH_3$, $(CH_2)_3—(CH=CH—CH_2)_3—(CH_2)_3—CH_3$, $(CH_2)_2—(CH=CH—CH_2)_4—(CH_2)_3—CH_3$, $(CH_2)_2—(CH=CH—CH_2)_5—CH_3$, and $CH_2—(CH=CH—CH_2)_6—CH_3$.

6. The compound of Formula I, according to claim 1, wherein R1, R2 and R3 each and independently, are selected from a group consisting of $(CH_2)_6—(CH=CH—CH_2)_2—(CH_2)_3—CH_3$, $(CH_2)_6—(CH=CH—CH_2)_3—CH_3$, $(CH_2)_3—(CH=CH—CH_2)_3—(CH_2)_3—CH_3$, $(CH_2)_2—(CH=CH—CH_2)_4—(CH_2)_3—CH_3$, $(CH_2)_2—(CH=CH—CH_2)_5—CH_3$, and $CH_2—(CH=CH—CH_2)_6—CH_3$.

7. A method for the production of a compound of Formula I, according to claim 1, wherein said method comprises:
A) reacting a 2-hydroxy fatty acid or sodium salt of a 2-hydroxy fatty acid and forming a 2-hydroxy-protected fatty acid of Formula III

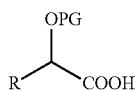

III wherein R is a hydrocarbon moiety which comprises an aliphatic chain containing between 5 and 22 carbon atoms and between 0 and 6 double bonds and PG is an alcohol protecting group;

B) reacting a glycerol and at least one 2-hydroxy-protected fatty acid of Formula III and forming a triglyceride of Formula IV

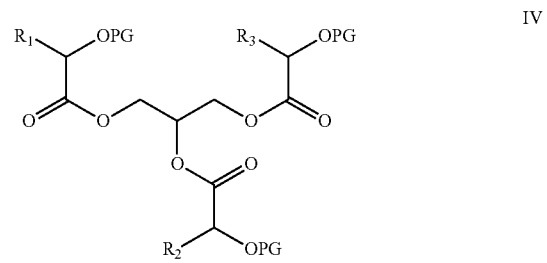

IV wherein R1, R2 and R3 are as defined in claim 1 and PG is an alcohol protecting group; and C) deprotecting the triglyceride of Formula IV obtained in the previous step.

8. A method of treating lung cancer and hypertension, said method comprising using a compound of Formula I according to claim 1.

9. The method according to claim 8, wherein R1, R2 and R3 each and independently, are selected from a group consisting of $(CH_2)_6—(CH=CH—CH_2)_1—(CH_2)_6—CH_3$, $(CH_2)_6—(CH=CH—CH_2)_2—(CH_2)_3—CH_3$, $(CH_2)_6—(CH=CH—CH_2)_3—CH_3$, $(CH_2)_3—(CH=CH—CH_2)_3—(CH_2)_3—CH_3$, $(CH_2)_2—(CH=CH—CH_2)_4—(CH_2)_3—CH_3$, $(CH_2)_2—(CH=CH—CH_2)_5—CH_3$, and $CH_2—(CH=CH—CH_2)_6—CH_3$.

10. A pharmaceutical and/or nutraceutical composition which comprises
a) at least one compound of Formula I, according to claim 1; and
b) at least one excipient.

11. A pharmaceutical and/or nutraceutical composition, which comprises
a) at least two different compounds of Formula I, according to claim 1; and
b) at least one excipient.

12. A method of preparation of a pharmaceutical and/or nutraceutical composition, which comprises mixing
a) at least one compound of Formula I, according to claim 1; and
b) at least one excipient.

* * * * *